United States Patent [19]
Ben-Bassat et al.

[11] Patent Number: 5,821,109
[45] Date of Patent: *Oct. 13, 1998

[54] RETICULATED CELLULOSE AND METHODS AND MICROORGANISMS FOR THE PRODUCTION THEREOF

[75] Inventors: Arie Ben-Bassat, Walnut Creek; Robert Bruner, El Cerrito; Sharon Shoemaker, Fairfield, all of Calif.; Yehoshua Aloni, Kfar-Saba, Israel; Harry Wong, San Leandro, Calif.; Donald C. Johnson, Auburn; Amar N. Neogi, Seattle, both of Wash.

[73] Assignee: Monsanto Life Sciences Co., Chicago, Ill.

[ * ] Notice: The term of this patent shall not extend beyond the expiration date of Pat. No. 5,079,162.

[21] Appl. No.: 442,597

[22] Filed: May 17, 1995

Related U.S. Application Data

[62] Division of Ser. No. 69,458, Jun. 1, 1993, which is a continuation of Ser. No. 683,304, Apr. 10, 1991, abandoned, which is a division of Ser. No. 196,496, May 19, 1988, Pat. No. 5,079,162, which is a continuation-in-part of Ser. No. 900,086, Aug. 28, 1986, abandoned, which is a continuation-in-part of Ser. No. 788,994, Oct. 18, 1985, abandoned.

[51] Int. Cl.$^6$ ............... C12P 19/04; C12P 1/04; C12N 1/20; C12N 1/00
[52] U.S. Cl. ............ 435/252.1; 435/101; 435/170; 435/823; 536/56
[58] Field of Search ................. 455/101, 170, 455/252.1, 823; 536/56

[56] References Cited

U.S. PATENT DOCUMENTS

| | | | |
|---|---|---|---|
| 4,320,198 | 3/1982 | Mynatt et al. | 435/101 |
| 4,378,431 | 3/1983 | Brown et al. | 435/101 |
| 4,588,400 | 5/1986 | Ring et al. | 604/304 |
| 4,929,550 | 5/1990 | Byrom | 435/101 |
| 5,079,162 | 1/1992 | Ben-Bassat et al. | 435/252.1 |

FOREIGN PATENT DOCUMENTS

| | | |
|---|---|---|
| 0114481 | 8/1984 | European Pat. Off. |
| 0186495 | 7/1986 | European Pat. Off. |
| 0200409 | 11/1986 | European Pat. Off. |
| 0206830 | 12/1986 | European Pat. Off. |
| 243151 | 10/1987 | European Pat. Off. |
| 0279506 | 1/1988 | European Pat. Off. |
| 0346507 | 12/1989 | European Pat. Off. |
| 0347481 | 12/1989 | European Pat. Off. |
| 8911783 | 12/1989 | European Pat. Off. |
| 8912107 | 12/1989 | European Pat. Off. |
| 088307 | 3/1972 | Germany |
| 237328 | 7/1986 | Germany |
| 212295 | 9/1986 | Japan |
| 87099 | 4/1987 | Japan |
| 1243997 | 9/1989 | Japan |
| 580595 | 9/1946 | United Kingdom |
| 1570487 | 7/1980 | United Kingdom |
| 2131701 | 6/1984 | United Kingdom |
| 8602095 | 4/1986 | WIPO |

OTHER PUBLICATIONS

Int. J. Biol. Macromol. 4: 244–246 (1982).
Int. J. Biol. Macromol. 7: 214–218 (1985).
Biochem, J. 50: 128–132 (1951).
Biochim. Biophys. Acta 3: 527–535 (1949).
The Microbial World 3rd Edition pp. 610–612, Prentice–Hall, Inc. 1978.
Polym. J. 7(2): 137–146 (1975).
Polymer Journal 7(2): 157–164 (1975).
Biochem. Biophys. Acta 338: 382–393 (1974).
Biochem. Biophys. Acta 177: 27–34 (1969).
Ann. Bot. 41: 455–460 (1977).
Biochem, J. 138: 537–542 (1974).
Antonie v. Leeuwenhoek 26: 169–181 (1960).
Hestrin et al., "Synthesis of Cellulose by Resting Cells of Acetobacter xylinum", Nature, vol. 159, pp. 64–65 (1947).
Hestrin and Schramm, "Synthesis of Cellulose by Acteobacter xylinum", vol. 58, pp. 345–352 (1954), Biochem. J.
Deley et al., in "Bergey's Manual of Systematic Bacteriology", Kreig and Holt, (Eds.) 1st Ed., Williams and Wilkins, Baltimore and London, pp. 267–278 (1984).
VanderHart et al., Science, 223:285–286 (1984).
VanderHart et al., Macromolecules, 17:1465–1472 (1984).
Schramm and Hestrin, "Factors Affecting Production of Cellulose at the Air/Liquid Interface of a Culture of Acetobacter xylinum" J. Gen. Microbiol., vol. II, pp. 123–129 (1954).
Leisinger et al., Arch. Mikrobiol. 54:21–36 (1966).
Svein Valla and Johs. Kjosbakken, "Cellulose–negative Mutants of Acetobacter xylinum, " J. Gen. Microbiol., vol. 128, pp. 1401–1408 (1982).
R.O. Couso et al., "Biosynthesis of Polysaccharades in Acetobacter xylinum,", Eur. J. Biochem., vol. 123, pp. 617–627 (1982).

(List continued on next page.)

Primary Examiner—David M. Naff
Assistant Examiner—Deborah K. Ware
Attorney, Agent, or Firm—Albert P. Halluin; Howrey & Simon

[57] ABSTRACT

A method and media for producing bacterial cellulose under agitated culture conditions resulting in sustained production over an average of 70 hours of at least 0.1 g/liter per hour are achieved. A unique reticulated cellulose II product is produced using the methods and conditions claimed, and may be in the form of a sheet characterized by resistance to densification and great tensile strength when produced by sheet forming means. Also strains of Acetobacter that are stable under agitated culture conditions and that exhibit substantially reduced gluconic and keto-gluconic acids production are described.

4 Claims, 4 Drawing Sheets

OTHER PUBLICATIONS

Dudman, "Cellulose Production by *Acetobacter acetigenum* and other Acetobacter spp.," *J. Gen. Microbiol.,* vol. 21, pp. 312–326 (1959).

Dudman, "Cellulose Production by Acetobacter Strains in Submerged Culture," *J. Gen. Microbiol.,* vol. 22, pp. 25–39 (1960).

Colvin, "The Formulation of Sperulites in Pellicles of Bacterial Cellulose," Canadian J. of Microbiol., vol. II, pp. 641–643 (1965).

Asai, *Acetic Acid Bacteria,* Chapt. 17, pp. 232–244 (1968), "Biosynthesis of Cellulose and Other Polysaccharides".

Haigh, *Biochem. J.,* 135:145–149 (1973), "Induction of Orientation of Bacterial Cellulose Microfibrils by a Novel Terpenoid from Acetobacter xylinum".

Brown, "Biogenesis of Natural Polymer Systems with Special Reference to Cellulose Assembly and Deposition," *Structure and Biochemistry of Natural Biological Systems,* E.M. Walk, (Ed.), (Philip Morris Co., N.Y) (1979).

Cook and Colvin, "Evidence for a Beneficial Influence of Cellulose Production on Growth of Acetobacter xylinum in Liquid Medium", *Current Microbiology,* vol. 3, pp. 203–205 (1980).

Aloni and Benzimen, "Intermediates of Cellulose Synthesis in Acetobacter", R.M. Brown (Ed.), *Cellulose and Other Natural Polymer Systems: Biogenesis Structure and Degradation,* pp. 341–361 (1982).

Brown, "Experimental Induction of Altered Nonmicrofibrillar Cellulose", *Science,* 218:1141–1142, (10 Dec. 1982).

Kai et al., "Appearance of microscopic fibrils in cellulose gel biosynthesized by Acetobacter xylinum" Nippon Kagaku Kaishi (3) pp. 536–537 (1982) (Abstr.).

Kai et al., "Study of the formation of bacterial cellulose microfibrils 2. Fibril formation in cellulose gels synthesized by Acetobacter xylinum", Nippon Kagaku Kaishi (8), pp. 1394–1399 (1982) (Abstr.).

Kai, "The Influence of Culture Conditions on the Fibrillation of Cellulose by Acetobacter Xylinum", *Bull. Chem. Soc. Jap.,* 57:2816–2819 (1984).

*C&EN,* "Studies shed more light on cellulose structure", p. 40, Sep. 23, 1985).

*The Japan Times,* p. 6, (May 18, 1987), entitled "Ajinomoto Co. Makes New Fiber".

Morrison & Boyd, "Organic Chemistry" Jun. 1978, pp. 1045–1046.

RETICULATED CELLULOSE AND METHODS AND MICROORGANISMS FOR THE PRODUCTION THEREOF

CROSS-REFERENCE TO RELATED APPLICATIONS

This application is a divisional of application Ser. No. 08/069,458, filed Jun. 1, 1993, now pending, which is a continuation of application Ser. No. 07/683,304, filed Apr. 10, 1991, now abandoned, which is a divisional of application Ser. No. 07/196,496, filed May 19, 1988, now issued as U.S. Pat. No. 5,079,162, which is a continuation-in-part of application Ser. No. 06/900,086, filed Aug. 28, 1986, now abandoned, which is a continuation-in-part of application Ser. No. 06/788,994, filed Oct. 18, 1985, now abandoned. Each of these applications is incorporated in its entirety by reference herein.

FIELD OF THE INVENTION

The invention concerns strains of Acetobacter that are capable of producing cellulose in artificial culture. More specifically, the Acetobacter strains according to the invention are characterized by an ability to produce large amounts of cellulose in agitated culture without manifesting instability leading to loss of cellulose production in culture. Among the Acetobacter strains according to the invention are strains additionally characterized by a substantially reduced ability to produce gluconic acid and keto-gluconic acids. The production of cellulose using such gluconate negative (glcA$^-$) strains in artificial culture medium, is facilitated as these strains do not substantially acidify the medium, and thus increase cellulose concentration (total gm/l) and volumetric productivity. Such gluconate negative Acetobacter strains are useful in high cell concentration cultures.

The invention also concerns a bacterial cellulose product having novel properties. In particular, the invention concerns a reticulated cellulose product. This reticulated bacterial cellulose product is characterized by a microscopic structure unlike that of bacterial cellulose produced by cellulose producing microorganisms under static culture conditions.

The invention also pertains to a method for producing the reticulated cellulose product by culturing cellulose producing microorganisms for sustained periods of time, generally in excess of four hours, under agitated culture conditions. The sustained and efficient production of bacterial cellulose under agitated culture conditions was unexpected.

BACKGROUND OF THE INVENTION

The production of cellulose by Acetobacter has been the subject of intense study since at least the 1930's. In 1947, it was shown that in the presence of glucose and oxygen, non-proliferating cells of Acetobacter synthesize cellulose. Hestrin, S., Aschner, M. and Mager, J., *Nature*, 159:64 (1947). Since the observations of Hestrin et al., Acetobacter has been grown with the production of cellulose under a variety of conditions. For example, when grown with reciprocal shaking at about 90–100 cycles per minute, cells have been incorporated into a large gel mass. When grown under conditions in which the culture medium is agitated with swirling motion for four hours, stellate gel bodies form which are comprised of cellulose and cells. When grown as standing-cultures, a pellicle forms at the air/medium interface. The pellicle forms as a pad generally having the same surface shape and area as the liquid surface of the vessel containing the culture. Hestrin and Schramm, *Biochem. Journal*, 58:345–352 (1954). Hestrin and Schramm observed rapid cellulose production by freeze-dried preparations of Acetobacter containing less than 10% viable cells. These experiments, however, only measured cellulose production in shaking conditions by such freeze dried preparations over a relatively short period of three to four hours, and were run under citrate buffering conditions to control significant pH changes caused by gluconic acid produced by Acetobacter in the presence of glucose.

Polysaccharide biosynthesis by Acetobacter has been studied by several groups using non-growing cultures. In some of these studies, Acetobacter strain 1499 was grown, the cells were freed from the cellulose pellicle, resuspended in 0.01M Tris-EDTA, frozen, and,then thawed as described in Hestrin and Schramm, (1954). These treated cells were used for biochemical studies under conditions that did not sustain growth of the cells, but which did preserve enzymatic activity permitting the cellulose to be synthesized by the prepared cells.

Progress in determining conditions for culturing Acetobacter for cellulose production, however, has not been the subject of wide reporting. Thus, the conditions used for culturing Acetobacter as described in U.K. patent application 2,131,701A, by Ring et al., which claims priority of U.S. patent application 450,324, filed Dec. 16, 1982 (now issued U.S. Pat. No. 4,588,400), are those described in Hestrin and Schramm (1954); i.e., an initial pH of about 6, temperatures in a range from 15° C. to 35° C. and preferably 20° C. to 28° C.

According to De Ley et al., "Acetobacteriacea" pp. 267–278 in *Bergeys Manual of Systematic Bacteriology*, Kreig and Holt, eds., 1st ed., William & Wilkins, Baltimore and London, 1984, the best carbon sources for growth in descending order are ethanol, glycerol and lactic acid. Acid is formed from n-propanol, n-butanol and D-glucose. The carbon sources described in U.K. application 2,131,701A include fructose, mannitol, sorbitol and glucose, all of which give rapid cellulose production, and glycerol, galactose, lactose, maltose and sucrose, all of which give slower growth. No growth was observed using sorbose, mannose, cellobiose, erythritol, ethanol, and acetic acid.

In U.K. patent application 2,131,701A it is desired to produce a coherent gel-like material for use as a wound dressing, after processing to remove the culture medium. To obtain this mat-like form, the culturing material is kept motionless during cell growth and cellulose production for a period ranging from a few hours to days or weeks.

Although the formation of a coherent mat or pellicle in motionless or standing culture conditions is the culture mode described in the U.K. patent application 2,131,701A, this patent further explains that intermittent agitation of the culture medium containing cellulose-synthesizing Acetobacter can control the length of the cellulose fibril produced by the microorganism. Intermittent agitation produces fibrils of finite length which is determined by the linear extension rate of the fibril by the microorganism and the period between agitative shearing of the fibril from the surface of the bacterium. Nothing, however, is disclosed about the effects of continuous agitation on the cellulose product.

The production of cellulose from Acetobacter in continuously agitated cultures is beset with numerous problems, the most difficult of which has heretofore been culture instability. This instability is demonstrated by loss of the ability to make cellulose and the gradual overgrowth of cellulose producing cells by non-producing types. Strain instability may be the result of the appearance of spontaneous mutants or variants of the microorganism that are cellulose non-producers. This appearance of non-producers apparently occurs with a frequency high enough to shift the population balance of a culture from cellulose-producing to cellulose non-producing types during growth in agitated culture. The loss of cellulose production in shaking cultures may also be merely the result of physiological factors rather than mutation to non-cellulose producing types due to genetic changes. Leisinger et al., Ueber cellulosefrie Mutanten von *Acetobacter xylinum, Arch. Mikrobiol,* 54:21–36 (1966). Although the cause is not known, the sustained production of bacterial cellulose in agitated culture medium has not heretofore been reported.

Cellulose negative (Cel⁻) strains of Acetobacter have been made by chemical mutagenesis with ethyl methane sulfonate (EMS), nitrous acid and N'-nitro-N-nitroso-guanidine (NG). When grown in static cultures, all of the EMS and nitrous acid-, and 90% of the NG-mutated strains reverted to cellulose producing types. Valla et al., Cellulose-Negative Mutants of *Acetobacter xylinum, J. Gen. Microbiol.*, 128(7):1401–1408 (1982). Growth of mixed cultures of cellulose producing and non-producing strains in static cultures strongly favored cellulose producing strains in static cultures, whereas growth of such mixed cultures in shake flasks favored non-producing strains. Valla et al. (1982). This result lends support to the hypothesis that the cellulose mat or pellicle produced by this microorganism enables Acetobacter cells to reach the surface of static liquid medium where the supply of oxygen is abundant. Under shaking conditions where oxygen dissolution rate and low oxygen solubility limits growth, cellulose negative strains are favored because of selective aggregation of cellulose producing cells and resulting mass transfer limitation with respect to oxygen. It will thus be readily apparent that the identification and isolation of Acetobacter strains that are stable cellulose producers in agitated culture medium is of critical importance to large scale production of cellulose from Acetobacter in cultures which are concentrated enough to require agitation for sufficient oxygen supply to the medium.

Acetobacter is characteristically a gram-negative, rod shaped bacterium 0.6–0.8 μm by 1.0–4 μm. It is strictly aerobic; metabolism is respiratory, never fermentative. It is further distinguished by the ability to produce multiple poly β-1,4-glucan chains, chemically identical to cellulose. Multiple cellulose chains or microfibrils are synthesized at the bacterial surface at sites external to the cell membrane. These microfibrils have cross sectional dimensions of about 1.6 nm×5.8 nm. In static or standing culture conditions the microfibrils at the bacterial surface combine to form a fibril having cross sectional dimensions of about 3.2 nm×133 nm.

The cellulose fibrils produced by these microorganisms, although chemically resembling, in many aspects, cellulose produced from wood pulp, are different in a number of respects. Chiefly among the differences is the cross-sectional width of these fibrils. The cellulose fibrils produced by Acetobacter are usually two orders of magnitude narrower than the cellulose fibers typically produced by pulping birch or pine wood. The small cross sectional size of these Acetobacter-produced fibrils, together with the concomitantly greater surface area than conventional wood-pulp cellulose and the inherent hydrophilicity of cellulose, leads to a cellulose product having unusually great capacity for absorbing aqueous solutions.

This capacity for high absorbency has been demonstrated to be useful in the manufacture of dressings which may be used in the treatment of burns or as surgical dressings to prevent exposed organs from surface drying during extended surgical procedures. Such uses and a variety of medicament impregnated pads made by treatment of Acetobacter-produced intact pellicles are disclosed in U.K. 2,131,701A. The pellicles of this U.K. application are produced by growing Acetobacter in a culture medium tray which remains motionless. Because Acetobacter is an obligate aerobe, i.e., it cannot grow in the absence of oxygen, production of cellulose by Acetobacter occurs at the air-liquid medium interface. Each bacterium continuously produces one fibril at the air-liquid interface. As new cellulose is formed at the surface, existing cellulose is forced downward into the growth medium. As a result, cellulose pellicles produced in static culture conditions consist of layers of cellulose fibers. Significantly, the volume of cellulose so produced is restricted by the interface between air and culture medium. The tendency of known Acetobacter strain's to become cellulose non-producers when cultured under agitated conditions at increased dissolved oxygen concentration, severely limits the amount of cellulose that can be made economically. Consequently, high cellulose productivity per unit volume of vessel in extended agitated fermentations has not been previously reported.

Another problem associated with cellulose production by Acetobacter in batch culture, whether agitated or motionless, is the ability of Acetobacter to convert glucose to gluconic acid and ketogluconic acids. The pH drop associated with such acid production by the organism also limits the amount of cellulose made, particularly in batch cultures. Moreover, the production of gluconic and keto-gluconic acids removes glucose from the medium at the expense of cellulose production.

Celluloses are encountered in various crystalline forms or "polymorphs." Celluloses have varying degrees of crystallinity depending on the source of the cellulose and method of treatment. Two common crystalline forms of cellulose are "cellulose I" and "cellulose II" which are distinguishable by X-ray, Raman spectroscopy and infrared analysis as well as by Nuclear Magnetic Resonance (NMR). Cellulose I is the lattice structure for native cellulose, and cellulose II is the lattice structure for mercerized or regenerated cellulose. Structural differences between cellulose I and II contribute to differences in reactivity and many physical properties of various celluloses.

In addition to cellulose I and II, celluloses typically have some amorphous regions which are present to some extent in all native, regenerated and mercerized celluloses and which complicate structural analysis.

C-13 solid-state NMR has revealed the presence of two distinct forms of cellulose I called I-alpha ($I_\alpha$) and I-beta ($I_\beta$). These forms occur in plant-derived celluloses as well as bacterial and algal celluloses. The $I_\beta$ form dominates in plant-derived celluloses whereas the $I_\alpha$ form dominates in algal and bacterial celluloses (VanderHart and Atalla, *Science* 223: 283–284 (1984), and VanderHart and Atalla, *Macromolecules* 17: 1465–1472 (1984)). These forms cannot be distinguished by X-ray diffraction but are clearly distinguishable by solid state C-13 NMR and Raman spectroscopy.

SUMMARY OF THE INVENTION

The present invention includes a reticulated bacterial cellulose product having novel properties. This reticulated bacterial cellulose product is characterized by a microscopic structure unlike that of bacterial cellulose produced by cellulose-producing microorganisms under static culture conditions.

The bacterial cellulose produced under known static culture conditions is characterized by a disorganized layered structure consisting of overlaying and intertwisted discrete cellulose strands or fibrils. This disorganized layered structure reflects the growth pattern of cellulose-producing microorganisms which is typified by the microorganism Acetobacter. In static cultures, Acetobacter typically grows at the interface of the surface of the liquid medium and air. As the cells grow, cellulose fibers are continuously elaborated and accumulated, sinking deeper into the medium. The cellulose pellicle thus formed is comprised of a mass of continuous layered cellulose fibers which support the growing population of Acetobacter cells at the air medium interface.

The macroscopic and microscopic structures of the cellulose produced in accordance with the agitated culture conditions of the invention differ from that made pursuant to the known static culture conditions. Macroscopically, the cellulose of the invention forms in the culture as pellets having diameters in the range of from approximately 0.05 mm to approximately 10.0 mm rather than as a continuous pellicle at the air medium interface. This pellet form remains after base extraction to recover the cellulose product and is believed to influence the physical properties of the final cellulose product. Microscopically (by scanning electron microscopy (SEM)), the cellulose product according to the instant invention is characterized by a three dimensional reticular structure. This structure is characterized by frequently thickened strands of cellulose that interconnect forming a grid-like pattern extending in three dimensions. The bacterial cellulose produced in static cultures is characterized by overlapping adjacent strands of cellulose that are oriented predominantly with the long axis of the strand in parallel but disorganized planes. By contrast, the reticular structure of the cellulose product according to the present invention is characterized by interconnecting, rather than overlapping strands of cellulose. These interconnecting strands have both roughly perpendicular as well as roughly parallel orientations. As a result, the reticular cellulose product according to the invention has a more generally fenestrated appearance in scanning electron micrographs, whereas cellulose produced in static culture has an appearance in scanning electron micrographs of strands piled on top of one another in a crisscrossing fashion, but substantially parallel in any given layer. The strands of the cellulose product according to the invention are generally thicker than those produced in comparable media without agitation. The reticulated cellulose was composed of interconnecting filaments ranging in width from about 0.1 to about 0.2 microns. The filaments or strands of cellulose produced under non-agitated conditions ranged in width from about 0.05 to about 0.2 microns with many strands in the range of 0.05 to 0.10 microns.

In addition, the fibrils of the non-reticulated cellulose product as compared to the fibrils of the reticulated product appear to branch and interconnect less frequently. Although the non-reticulated cellulose product appears to have many fibrils that contact one another, the fibrils overlay one another rather than interconnect. By contrast, the fibrils of the reticulated cellulose according to the invention, have a large proportion of fibers that interconnect or intertwine to form a substantially continuous three-dimensional network of interconnecting fibers.

The reticulated cellulose product according to the invention has several advantages over cellulose produced under non-agitated conditions. Because the reticulated cellulose product is characteristically produced in agitated cultures of cellulose producing microorganisms such as Acetobacter, it can be produced using conventional high volume fermentation methods. Thus, unlike the production of cellulose pellicles in the slow growing, non-agitated culture media of the prior art, the reticulated cellulose product of the present invention may be produced in fast growing cultures of Acetobacter with high volumetric productivity and high concentration of the reticulated cellulose product.

One way the reticulated cellulose product according to the invention can be distinguished from bacterial cellulose produced under non-agitated conditions is by its characteristics upon consolidation into a paper-like sheet. Batches of the reticulated cellulose product generally offer a high resistance to densification when formed into a sheet by conventional means. By use of different wet pressing loads, a series of sheets was prepared having densities in the range of about 300 to about 900 kg/m$^3$, with those exhibiting substantial resistance to densification being about 300 to about 500 kg/m$^3$. In spite of the low densities, these paper like sheets have very high tensile strength as measured according to Technical Association of the Pulp and Paper Industry (TAPPI) method T494 om-81 using an Instron Universal test instrument. Typically, the tensile index for sheets made from reticulated cellulose of the density range of 300–500 kg/m$^3$ is between 100 and 150 Newton-meters/gram. Comparable sheets formed from kraft pulp having densities below about 500 kg/m$^3$ have virtually no tensile strength.

Handsheets formed from cellulose produced under static culture conditions do not exhibit the above-mentioned resistance to densification. Typically, such sheets from non-agitated cultures of cellulose have densities from about 500 to about 750 kg/M$^3$ depending on the wet pressing load employed.

The invention also pertains to a method for producing the reticulated cellulose product by culturing cellulose producing microorganisms for sustained periods of time under agitated culture conditions. The production of bacterial cellulose under agitated culture conditions is surprising in light of the well known tendency of agitated culture conditions to select for cellulose non-producing strains of Acetobacter. Valla et al., (1982). Moreover, the reticulated structure of the cellulose produced under these conditions is entirely unexpected.

As used herein, the term Acetobacter refers to a genus of microorganisms, and in particular, to the members of that genus that produce cellulose. Although a number of microorganisms fitting this description are known, their taxonomic classification has been subject to debate. For example, the cellulose producing microorganisms listed in the 15th Edition of the catalogue of the American Type Culture Collection under accession numbers 10245, 10821, and 23769 are classified both as *Acetobacter aceti subsp. xylinum* and as *Acetobacter pasteurianus*. Thus, any cellulose producing strain of Acetobacter whether classified as *Acetobacter aceti subsp. xylinum, Acetobacter pasteurianus* or otherwise, that has the characteristics of stability under agitated culture conditions as further explained below, is considered to be within the scope of the invention.

The inventors have discovered and developed a number of strains of Acetobacter that are stable in long term cultures under both non-agitated and agitated culture conditions including fermentor process conditions. The stability of the strains is demonstrated under agitated conditions; the strains according to the invention generally appear to change to cellulose non-producing types at a very low frequency, on the order of less than 0.5% at the end of a fermentation run of 42–45 generations (including the seed and pre-seed stages), as determined by colony morphology when subcultures of Acetobacter grown in liquid medium under agitated conditions are plated on solid medium.

The Acetobacter strains according to the invention have been mutagenized and a number of derivative strains have been selected. At least two of the selected strains are characterized by a sharply reduced ability to form gluconic and keto-gluconic acids when grown on a glucose containing medium. Such strains having a reduced ability to form gluconic acid are stable. At the end of a fermentation run of 42–45 generations (including the seed and pre-seed stages), less than 0.5% gluconic and ketogluconic acid producing types are detected as determined by the inability of cells from the fermentor broth to form calcium carbonate-clearing colonies on agar plates containing glucose. These strains are stable with respect to change to cellulose non-producing type and to change to gluconic and keto-gluconic acids producing type.

Various feed stocks may be used as the carbon source for growth of the cellulose-producing microorganisms and reticulated cellulose product according to the invention so long as they are supplied free of contaminating organisms. Appropriate carbon sources include the monosaccharides and disaccharides in pure or partially purified form or as monosaccharide and disaccharide-containing stocks such as hydrolyzed corn starch, hydrolyzed wood and molasses.

Cellulose production with the strains according to the invention may be carried out under conditions permitting higher dissolved oxygen concentration than possible under standing conditions. The ability of the strain to maintain cellulose production while agitated permits various means for increasing dissolved oxygen in the culture medium to be used. Thus, direct agitation of the culture medium by impellers immersed in the medium has been used successfully, although adherence of the cellulose produced to the impeller blades can be a disadvantage for small-scale production. Means for agitating the culture which increase dissolved oxygen content are well known to those familiar with microbial fermentation. Oxygen tension in the broth can vary between 0.01 to 1.0 atmosphere oxygen.

In tests in a fermenter (14 liters) using an impeller to agitate the broth, it was found that the characteristics of the broth (viscosity) and the resulting cellulose (particle size and morphology, settling rate, hand sheet formation) are affected by high impeller speeds (above about 600 rpm in the runs carried out). These effects were more pronounced the longer the cultures were agitated at such speeds. It is not known whether these results will apply to all fermenter volumes and configurations and/or methods of agitation. In the tests conducted, however, the higher impeller speeds/longer agitation times resulted in smaller particles determined by longer particle settling times, higher suspension viscosity, less cellulose retained in handsheet tests. Accordingly, depending on the intended end use for the cellulose, it may be desirable to avoid culturing the organisms under such extreme agitation conditions. It is, therefore, preferred to carry out the fermentation at sufficiently low agitation rates and agitation times so as to avoid any substantial degradation of the properties of the cellulose product.

The effective pH range for culturing the cellulose producing microorganisms according to the invention is between 4 and 6, with a preferred range of 4.5 to 5.5, and most preferably pH 5. pH may be controlled by means of buffers such as citrate or 3,3 dimethylglutaric acid added to the culture medium; or the addition of base or, acid to the medium in an amount sufficient to maintain pH in the desired range.

BRIEF DESCRIPTION OF THE DRAWINGS

FIG. 1A shows the product before base extraction; FIG. 1B shows it after base extraction and purification. The dividing lines are approximately 1 mm apart.

DETAILED DESCRIPTION OF THE INVENTION

Figure 1A:
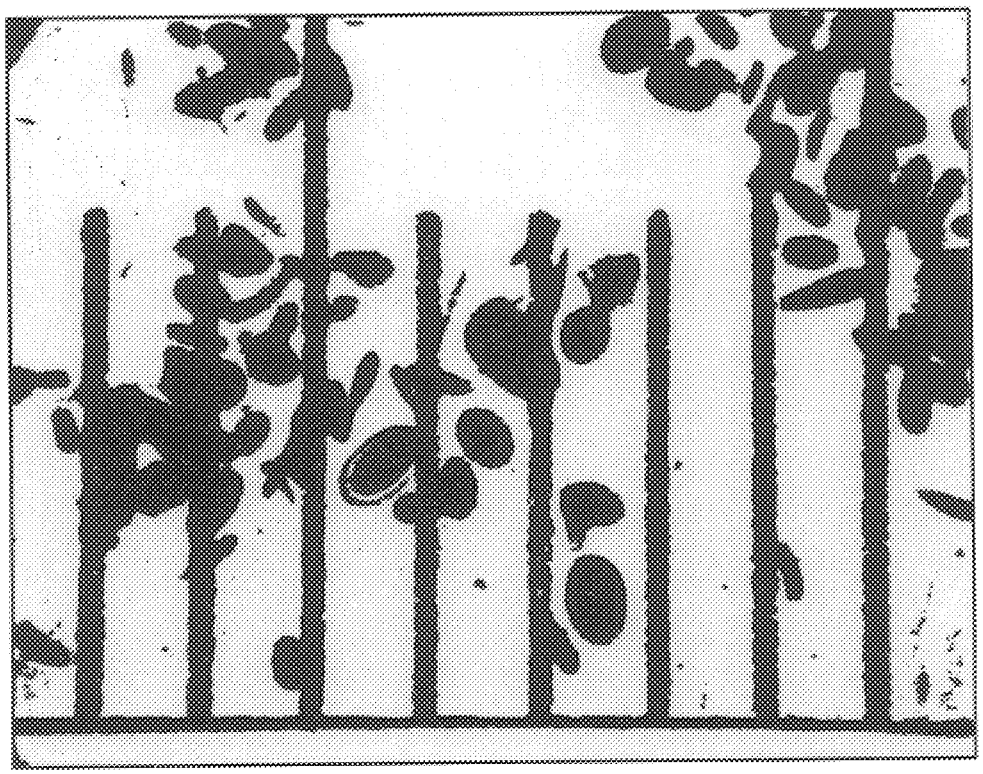
FIGS. 1A and 1B are photographs showing the macroscopic structure of the reticulated cellulose product in pellet form of the present invention.

In the following detailed description of the invention a number of culture media are mentioned. Unless otherwise indicated the media are formulated as is indicated below.

R20-2 medium has the following composition:

| R20-2 | |
|---|---|
| Bacto-peptone | 5 g/l |
| Yeast Extract | 5 g/l |
| $Na_2HPO_4$ | 5 g/l |
| Citric Acid | 1.15 g/l |
| Carbon Source | As specified (if not specified, 2% glucose) |
| Final pH | 5.0 +/− 0.2 |

R20 is the same as above but the final pH is 6.0. R20-3 is the same as above but citric acid is omitted.

Y-1 medium, also referred to as minimal medium R70 or Acetobacter Minimal Medium (AMM), has the following composition:

| Compound | Final Concentration (mM) |
|---|---|
| $(NH_4)_2SO_4$ | 25 |
| $KH_2PO_4$ | 7.3 |
| $MgSO_4$ | 1.0 |
| $FeSO_4$ | 0.013 |
| $CaCl_2$ | 0.10 |
| $Na_2MoO_4$ | 0.001 |
| $ZnSO_4$ | 0.006 |
| $MnSO_4$ | 0.006 |
| $CuSO_4$ | 0.0002 |
| | pH = 5.0 |
| Glucose | 2% or 4% (w/v) unless otherwise specified |

For all studies using Y-1 medium the following vitamin mix was added to the minimal medium at a 100 fold dilution:

| Vitamin Mix | |
| --- | --- |
| Compound | mg/L |
| Inositol | 200 |
| Niacin | 40 |
| Pyridoxine HCl | 40 |
| Thiamine HCl | 40 |
| Ca Pantothenate | 40 |
| Riboflavin | 20 |
| Para-aminobenzoic acid | 20 |
| Folic Acid | 0.2 |
| Biotin | 0.2 |

Corn steep liquor (CSL) medium has the following composition:

| Ingredient | Final Concentration (mM) |
| --- | --- |
| $(NH_4)_2SO_4$ | 25 |
| $KH_2PO_4$ | 7.3 |
| $MgSO_4$ | 1.0 |
| $FeSO_4$ | 0.013 |
| $CaCl_2$ | 0.10 |
| $Na_2MoO_4$ | 0.001 |
| $ZnSO_4$ | 0.006 |
| $MnSO_4$ | 0.006 |
| $CuSO_4$ | 0.0002 |
| vitamin mix (above) | 10 ml/liter |
| carbon source | as specified (usually glucose 2 or 4%, w/v) |
| corn steep liquor (supernatant fraction after centrifugation) | as specified (usually 2 or 5%, v/v) |
| Antifoam | 0.01% (v/v) |
| final pH = 5.0 ± 0.2 | |

The composition of corn steep liquor varies depending on supplier and mode of treatment. A typical corn steep liquor sample, Type E804 obtained from Corn Products Unit, CPC North America, Stockton, Calif. is described below:

| Major Components | Percent |
| --- | --- |
| Solids | 43.8 |
| Crude protein | 18.4 |
| Fat | 0.5 |
| Crude fiber | 0.1 |
| Ash | 6.9 |
| Calcium | 0.02 |
| Phosphorous | 1.3 |
| Nitrogen free extract | 17.8 |
| Non-protein nitrogen | 1.4 |
| NaCl | 0.5 |
| Potassium | 1.8 |
| Reducing sugars (as dextrose) | 2.9 |
| Starch | 1.6 |
| pH | 4.5 |

Y3-3 medium has the following composition:

| Component | Concentration |
| --- | --- |
| Yeast extract | 10 g/l |
| Peptone | 10 g/l |
| $KH_2PO_4$ | 4 mM |
| $K_2HPO_4$ | 6 mM |
| Glucose | 20 g/l |
| pH | 6.0 |

R70-2 medium is a modified form of AMM. R70-2 has the following composition:

| Ingredient | Final Concentration (mM) |
| --- | --- |
| $(NH_4)_2SO_4$ | 25 |
| $KH_2PO_4$ | 7.3 |
| Na Citrate | 4.0 |
| $MgSO_4$ | 1.0 |
| $FeCl_3$ | 0.01 |
| $CaCl_2$ | 0.10 |
| $Na_2MoO_4$ | 0.001 |
| $ZnSO_4$ | 0.005 |
| $MnSO_4$ | 0.005 |
| $CuSO_4$ | 0.001 |
| $COCl_2$ | 0.001 |
| $NiCl_2$ | 0.001 |
| vitamin mix (see below) | 10 ml/liter |
| Glucose | as specified (usually 2 or 4%, w/v) |
| final pH | 5.0 ± 0.2 |

| Vitamin Mix | |
| --- | --- |
| Compound | mg/l in mix |
| Inositol | 200 |
| Niacin | 40 |
| Pyridoxine HCl | 40 |
| Thiamine HCl | 40 |
| Ca Pantothenate | 40 |
| Riboflavin | 20 |
| PABA | 20 |
| Folic Acid | 0.2 |
| Biotin | 0.2 |

One aspect of the invention concerns a number of stable cellulose producing strains of Acetobacter. The stability of Acetobacter strains according to the invention is demonstrated by a very low frequency of conversion to phenotypes that do not produce cellulose. The frequency of conversion to phenotypes that do not produce cellulose is less than $5 \times 10^{-3}$ as determined by colony morphology when subcultures of Acetobacter grown under agitated conditions are plated on solid medium at the end of a fermentation cycle of 42–45 generations. The colonies of the cellulose-producing strains on solid medium are generally beige or white and are small, raised or convex and compact in size. By contrast cellulose non-producing strains form large, usually flat colonies on solid medium. In addition to Acetobacter other cellulose producing bacteria such as organisms in the genus Agrobacterium may be fermented in agitated culture to produce cellulose as described herein.

The stable Acetobacter strains according to the invention were derived from an initial isolate of an *A. xylinum* strain obtained from the Northern Regional Research Laboratory, Peoria, Ill. USA under Accession No. NRRL B42. Growth of the NRRL strain on agar plates of R20-2 medium revealed two colony morphologies, one white, the other beige. Microscopically, the beige colonies have the elongated rod shape cells typical of the Acetobacter strain. This strain is designated 1306-3. Unlike the parent NRRL B42 strain, 1306-3 produces no water soluble polysaccharide as reported by Couso, R. O. et al., Biosynthesis of Polysaccharides in *Acetobacter xylinum*; Sequential Synthesis of a Heptasaccharide Diphosphate Prenol; *Eur. J. Biochem.* 123:617–627 (1982). Cultures of 1306-3 are stable in both microscopic morphology and macroscopic colony morphology when subcultured on different media containing a variety of carbon sources. Furthermore, colony and cellular morphology of the strain according to the invention remain stable whether grown in static or shaking liquid cultures in various media.

Strain 1306-3 and its progeny are capable of producing cellulose in a variety of liquid culture media having various carbon and nitrogen sources. Casein hydrolysate, protein hydrolysate, yeast extract, malt extract, ammonium salts, corn steep liquor and other nitrogen-rich substances can be used as a general source of amino acids, nitrogen, minerals and vitamins. Corn steep liquor is preferred in a range between 0.1% and 10% (v/v). 3% (v/v) corn steep liquor is preferred for shaking flask cultures. In fermentors an initial concentration of 2% (v/v) corn steep liquor is supplemented during the fermentation run with an additional 2% (v/v) corn steep liquor. Numerous carbon sources may be used including mannitol, sorbitol, sucrose, fructose and glucose, although using the latter carbon source, D-gluconic acid and ketogluconic acids, including 2-keto-D-gluconic acid or 5-keto-D-gluconic acid, are produced by strain 1306-3.

Acetobacter strains according to the invention that produce significantly lower amounts of D-gluconic acid have also been developed by the inventors and are further described herein below.

Carbon sources useful in the production of the reticulated cellulose product may be characterized as monosaccharides or mixtures thereof such as glucose and fructose, disaccharides such as sucrose, and mixtures of monosaccharide and disaccharides. In addition, the carbon source can be supplied as a complex mixture of sugars such as molasses, or plant biomass hydrolysates such as wood hydrolysate, straw hydrolysate, corn stalk hydrolysate, sorghum hydrolysate and the like.

The concentration of monosaccharides and disaccharides or mixtures thereof may vary. Glucose alone and fructose alone in a range of 0.5 to 7% (w/v) with a preferred concentration of about 4% (w/v) have been used. In addition, mixtures of glucose and sucrose in a ratio from 1:10 to 10:1 (w/w) having a total of 0.5 to 7% (w/v) of the medium may be used. A concentration of 1% (w/v) glucose and 2% (w/v) sucrose is preferred in flask cultures. In fed batch fermentation in which the carbon source is intermittently or continuously supplied during fermentation, the total carbon substrate added can vary between 4 to 30% (w/v). The carbon source may be supplied as a purified or partially purified feed stock or alternatively as a complex mixture such as molasses. Such carbon sources are pretreated so that they are free of contaminating organisms.

The conversion of glucose to D-gluconic acid on glucose containing medium leads to a significant drop in pH of the medium in batch culture. Since pH below about 4.0 may limit growth of the cells, pH control is desirable. pH control in liquid media culture of gluconic acid producing strains according to the invention can be effected by use of buffers such as citrate. However, the amount of buffer that can be added to neutralize the acid is limited and growth of gluconate-producing strains to high density is limited by the amount of buffer which can be added. In addition, the use of citrate or other salts as buffers adds to the expense of the culture medium. pH control can also be effected by using fructose as the carbon source, since Acetobacter does not metabolize fructose to acid. However, fructose is an expensive substrate and increases the production cost of the cellulose fiber.

By treating strain 1306-3 with a mutagen, the inventors have developed stable variant strains exemplified by strains 1306-11 and 1306-21. These strains produce significantly reduced amounts of gluconic acid, and keto-gluconic acids yet produce cellulose in a stable manner typical of the parent strain 1306-3. Mutagenesis was accomplished using a concentration of ethyl methane sulfonate (EMS) sufficient to yield a survival rate of approximately 1%. In the case of strain 1306-11 of the surviving mutagenized bacteria, 8100 colonies were screened. Two isolates produced reduced amounts of gluconic acid and keto-gluconic acids.

Strain 1306-11 was selected by culturing on plates of R20-$CaCO_3$ medium and screening for colonies having a morphology similar to the parent strain 1306-3 but which do not clear calcium carbonate in the medium. Other pH sensitive assays capable of detecting the absence of pH reducing substances such as gluconate can also be used.

Strain 1306-21 was selected as described in Example V, infra.

Bacterial cultures may be grown under agitated culture conditions by any means known to generate turbulence in the liquid culture medium. Such means are well known to those skilled in the fermentation arts. At small scale, generally less than 1 liter culture volume, liquid cultures may be agitated by reciprocal or shaking incubators, which impart a swirling motion to the medium.

Various reactor designs may be appropriate for the large scale production of the cellulose product according to the invention. See, e.g., Chapter 7 of *Biochemical Engineering and Biotechnology Handbook*, Atkinson and Mavituna, eds., 1st Ed. The Nature Press, New York, 1983. For large scale cellulose production, generally culture volumes exceeding 1 liter, the culture broth may be agitated by a number of means including various types of impellers, buoyant lift fermentors including air lift fermentors, pump driven recirculation of the fermentor broth or combinations thereof. Desirable characteristics for the fermentor impellers include high mass transfer rates, high circulation rates and low shear stress.

So long as the culture medium is agitated, various fermentation methods are appropriate for growing the cellulose producing microorganism at an average volumetric productivity for cellulose, which is within the scope of the invention, of at least 0.1 g/l/hr for sustained periods of time. Appropriate fermentation methods include batch fermentation, fed batch fermentations, repeated batch fermentation, and continuous fermentation. In batch fermentations the cellulose-producing microorganism is inoculated into a fermentation vessel and the fermentation proceeds without further addition of culture media. At the end of the fermentation, the contents of the fermentation vessel are collected and the cellulose is removed. In fed batch fermentations, various nutrients, such as carbon source or nitrogen source are added to the medium during the fermentation run without removing the fermentation broth for processing until the end of the fermentation run. The nutrients may be added continuously, at predetermined intervals or when nutrient levels in the medium fall below desired values. In repeated batch fermentations, a volume of the culture broth is removed for processing, a volume of fresh medium is added to the culture broth remaining in the culture vessel, and the fermentation is resumed. In repeated batch fermentations, as in fed batch fermentations, the nutrients may be added continuously, at predetermined intervals or when nutrient levels in the medium fall below desired values. In continuous fermentations, the broth is removed from the fermentation vessel and replaced with fresh medium at a constant rate. In continuous fermentations, by adjusting the flow of medium into and culture broth out of the vessel, the specific growth rate of the cellulose producing microorganism can be maintained at an approximately constant rate.

Batch fermentations, fed batch fermentations, repeated batch fermentations, and continuous fermentations are all suitable for achieving an average volumetric productivity of at least 0.1 g/l/hr. so long as the inoculum of the culture medium is initially at least 1% (v/v). An inoculum in a range of 1–10% (v/v) of the culture medium is effective to obtain an average volumetric productivity of cellulose of 0.1 g/l/hr. An inoculum of about 5–10% (v/v) of the culture medium is preferred. In continuous cultures, as medium, cellulose-producing cells and cellulose are removed, fresh medium will be added at a rate sufficient to maintain the volumetric productivity at an average of at least 0.1 g/l/hr.

Figure 1B:
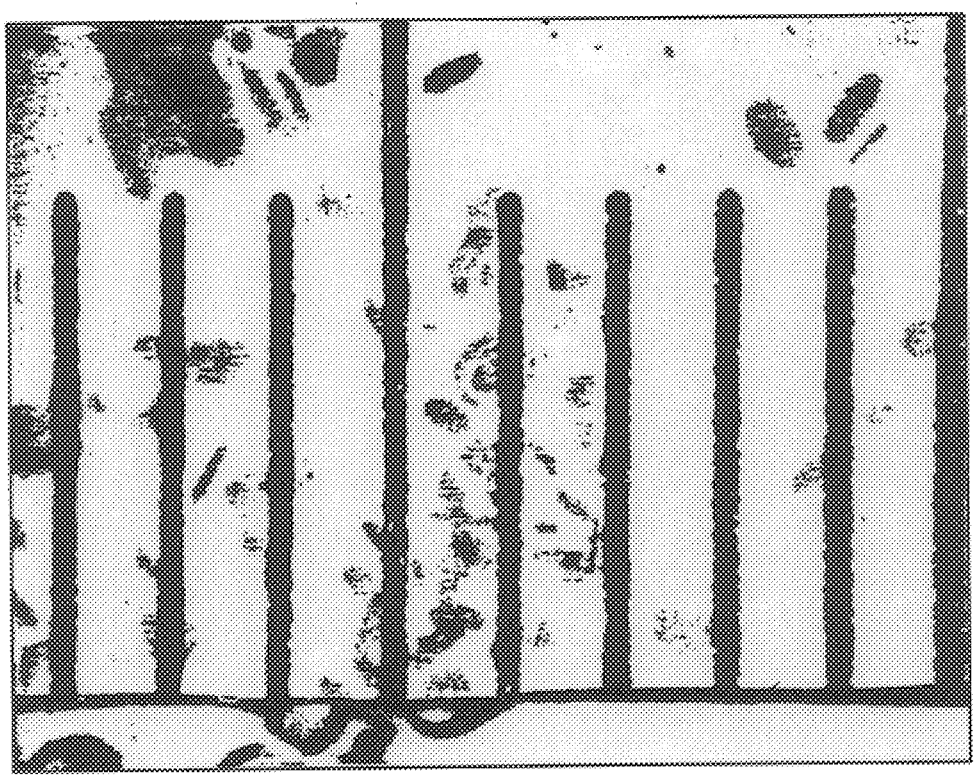

To determine cellulose concentration and volumetric productivity, cellulose produced by any of the above mentioned fermentation methods is harvested from the fermentation broth. In general, any method for separating the cellulose may be used, but centrifugation is preferred. Each batch of fermentation broth containing the cellulose-producing microorganism, used medium, and cellulose, is centrifuged. The volume of the supernatant medium is determined and the supernatant is discarded. The pellet comprising solid matter including the microorganisms and cellulose is retained. The pellet is washed several times with deionized water to remove residual medium. FIG. 1A shows the macrostructure of the pellet at this stage. The retained matter is treated with an alkali solution such as 0.1M NaOH or KOH at 60°–65° C. for at least two hours. The suspension may be mixed to disperse large clumps of cellulose. During the alkali treatment, the mixture is slowly stirred and maintained at 60°–65° C. The alkali treated material is centrifuged and the pellet is then washed and centrifuged three or four times in deionized water. FIG. 1B shows the macrostructure of the cellulose at this stage. The cellulose is then dried in a vacuum oven and is weighed. Volumetric productivity is defined as total mass of cellulose produced per volume of medium used per fermentation time (g/l/hr) from inoculation to harvest for batch cultures.

The form of the cellulose, such as that shown in FIGS. 1A and 1B is dependent on the growth and hydrodynamic conditions in the fermentor used, and in the case of FIG. 1B also depends on the hydrodynamic and other physical conditions during purification and recovery of the cellulose. The important hydrodynamic factors affecting the form and quality of the cellulose product, such as effects on pellet morphology and size and the ability to make handsheets, include shear stresses; normal stresses; turbulent eddy stresses; and pressure and cavitation forces during fermentation, purification and recovery. These factors in turn are dependent on the size and configuration of the vessels used; the type of impellers used; the agitation rates; the gas sparge rates; the temperature of the cellulose broth; the pH of the cellulose broth; the pressure to which the cellulose broth is subjected; the rheology of the cellulose broth; composition and total mass of the cellulose broth; the pumps and other means of transporting the cellulose broth used; and the time under the above conditions.

In addition to scanning electron microscopy, the structure of the reticulated cellulose of the invention produced in agitated culture may be investigated and compared to that of cellulose produced in static culture using C-13 NMR spectra. In order to analyze the various forms of cellulose, it was necessary to develop suitable NMR reference spectra for three crystalline forms of cellulose, $I_\alpha$, $I_\beta$ and II. A spectrum for cellulose II was generated from a sample of highly crystalline cellulose II. Whatman CF-1 filter paper is derived from cotton and is known to have a high $I_\beta$ content, whereas bacterial cellulose has a high $I_\alpha$ content. The reference spectra for $I_\alpha$ and $I_\beta$ were generated by the procedure described by VanderHart et al., *Macromolecules*, supra, incorporated by reference herein, by subtracting an appropriately scaled spectrum obtained by NMR analysis of Whatman CF-1 hydrocellulose powder from the spectrum obtained for cellulose sample A-012-6 (from non-agitated culture, Acetobacter strain 1306-8) to generate the cellulose $I_\alpha$ spectrum, and subtracting a fraction of a scaled A-012-6 spectrum from the CF-1 spectrum to generate the $I_\beta$ spectrum. This approach successively eliminates the IS and $I_\alpha$ components. These reference spectra may then be used to determine the $I_\alpha$, $I_\beta$ and cellulose II components of each bacterial cellulose sample (agitated and static) by obtaining the NMR spectrum for a sample of bacterial cellulose, then successively subtracting the reference spectra. The remaining NMR signal and its total intensity represents largely the amorphous cellulose after correcting for the residual signal at 90 PPM. The amorphous cellulose content is then independently verifiable by analysis of the C-4 resonance of the original cellulose spectrum which has distinguishable crystalline and amorphous components. In addition, there is a residual component peak that is not accounted for by the other four components and represents a minor impurity present in nearly all of the samples.

Using this C-13 NMR methodology, the structures of samples of bacterial cellulose produced under agitated conditions were compared to the structure of samples produced under static culture as described below in Example XIX. Reticulated bacterial cellulose from agitated cultures exhibited a microstructure significantly different from that of cellulose produced in static culture.

The following examples are merely to be exemplary of the invention and are not intended to be limiting.

EXAMPLE I

Cellulose Production in Static Culture

This example shows cellulose production by *A. xylinum* 1306-3 growing on fructose as the main substrate under non-shaking conditions. In this example (and examples II and XI) fructose was used instead of glucose to avoid acidification of the media by acid producing Acetobacter strains from oxidation of glucose to gluconic acid and keto-gluconic acids. Strain 1499-1 obtained from Dr. Moshe Benziman, Hebrew University, Jerusalem, Israel was grown under identical conditions for purposes of comparison.

Seed flasks were set up containing 25 ml of Y3-3 medium with 2% fructose in 50 ml Erlenmeyer flasks and were inoculated from agar slants. The cultures were grown for three days at 30° C. as standing cultures. The flasks were vigorously shaken by hand to release cells and 0.5 ml of this culture (without cellulose pellicle) was inoculated into several flasks of identical Y3-3 medium with 2% w/v fructose (25 ml in 50 ml flasks). Equal inoculation of all strains was accomplished using 0.03 OD at 670 nm cell suspension and inoculating 0.5 ml into each flask. The flasks were incubated at 30° C. without shaking.

Flasks were removed from incubation and the entire contents were harvested for sampling. Each strain was sampled in duplicate at each time point. Sampling was started when growth was evident and two samples were normally taken each day.

To measure cellulose production, the flask contents of each sample were transferred to a 100 ml beaker. The suspension was then macerated for one minute with a large Tekmar probe at 50% of full power. The suspension was centrifuged at 5,000 rpm for 10 minutes. The supernatant was discarded and the pellet was resuspended in 15 ml 1.0N NaCl saline and vortexed. The suspension was allowed to equilibrate for 15 minutes with occasional vortexing. The sample was again centrifuged and the above wash step repeated.

The pellet from the second wash was resuspended in 15 ml of 0.5N KOH and incubated at 60° C. with mild agitation for 120 minutes. The suspension was centrifuged and the KOH supernatant discarded. The pellet was resuspended in 15 ml deionized $H_2O$ and left at room temperature to equilibrate for 15 minutes with occasional vortexing. The sample was centrifuged and the above wash procedure was repeated for a total of four washes.

After the last centrifugation step the wet cellulose mat was dried at 55° C. under vacuum overnight and then weighed.

TABLE 1

| Strain | Time (hr) | Cellulose (g/l) | | | | | |
|---|---|---|---|---|---|---|---|
| | | 30 | 60 | 114 | 138 | 162 | 234 |
| CMCC 1306-3 | | 0.34 | 0.94 | 1.1 | 1.3 | 1.6 | 2.66 |
| CMCC 1499-1 | | N.D. | 0.19 | 0.51 | 0.67 | 0.72 | 1.30 |

Cellulose production by strain 1306-3 and strain 1499-1 on Y3-3 medium with 2.% fructose. The initial pH was 6.0,
N.D. = Not determined

EXAMPLE II

Cellulose Production in Agitated Cultures Stability Studies

The stability of cellulose synthesis in strains 1306-3 and 1499-1 was examined during serial transfers of the strains in liquid agitated cultures, using a homogeneous (well mixed) inoculum in each transfer. Observation of cellulose production in the flasks and appearance of large colonies (L-colonies) from samples on plates was used to evaluate the stability of cellulose synthesis. Cellulose production in 1499-1 appeared to be unstable in aerobic agitated flasks as is shown by a reduction in the amount of cellulose produced and the appearance of increasing numbers of large diffuse colonies which represent cellulose non-producers. Cellulose production in 1306-3 appears to be stable for at least 30 generations in agitated flasks.

Seed cultures were inoculated from agar slants of the parental culture into 25 ml of R-20 medium with 2% fructose at pH 5.0 in 50 ml Erlenmeyer flasks. The seed culture was grown for four days at 30° C. as a standing culture. The flasks were shaken vigorously by hand to release cells and 0.5 ml of this culture (without cellulose pellicle) was inoculated into several flasks of the R20 medium with 2% fructose (25 ml in 50 ml flasks). These flasks were incubated at 30° C. without shaking.

After several transfers in standing flasks the 36 hour pellicle was vigorously shaken and the supernatant was used as inoculum (1% v/v) to the flasks containing R20 with 2% fructose, pH 5. The flasks (25 ml medium in 125 ml flasks) were incubated at 30° C. and at 200 rpm in a New Brunswick gyratory shaker. After 24 to 48 hours the culture was aseptically blended and used as inoculum for second transfer into fresh medium and for streaking on plates. Each strain was examined for four transfers which is roughly equal to 30 generations. The medium used for plate experiments was R20 with 2% fructose, 1.5% agar, pH 5.0.

During growth in shake flasks the culture of strain 1499-1 appeared as a fine suspension of cells and irregular clumps of different sizes. The ratio of clumps to cell suspension decreased from first transfer to the third transfer. This observation was correlated with a significant decrease in the amount of cellulose produced from first transfer to the third transfer, and an increase in the fraction of L-colonies which represent cellulose-non-producing strains.

The frequency of L-colonies in strain 1499-1 as a function of growth is shown in Table 2.

TABLE 2

| Instability of strain 1499-1 in agitated culture | |
|---|---|
| Stage | % L- forms |
| Stock | 8.5 |
| Inoculum to shake flasks | 8.0 |
| End of first shaking stage | 18.0 |
| End of third shaking stage | 33.0 |

In sharp contrast, strain 1306-3, during growth in shake flasks, appeared as irregular clumps of different sizes with clear medium between them. Cellulose negative cells appear as single cells in the broth and cause turbidity in the medium between the clumps. No changes in the culture appearance or in the amount of cellulose produced were observed after four transfers. During that time the colonies on plates appeared to be homogeneous; no large, non-producing colonies were observed.

EXAMPLE III

Mutagenesis of Strain 1306-3

Acetobacter strain 1306-3 was mutagenized with 1% or 2% of the chemical mutagen ethyl methane sulfonate (EMS) and the surviving cells were screened for loss of the ability to produce gluconate (glcA–) and keto-gluconates. Two glcA– isolates were obtained. The mutagenesis was carried out as follows:

Two day old culture of 1306-3 on R20-2 medium was used for the mutagenic treatment. Conditions were chosen to give about 99% kill. The conditions selected were 0.1M potassium phosphate buffer, pH 6.0; 2% EMS and incubation at 28° C. for 60 minutes. Cell concentration was approximately $5 \times 10^7$ cells/ml. After this treatment the culture was kept frozen at –80° C. for further use.

EXAMPLE IV

Screening for Gluconate Negative Mutants

Screening to obtain gluconate negative mutants of Acetobacter strain 1306-3 was done with the culture obtained from the EMS mutagenesis described in Example III. Screening was done on R20-2 agar plates containing 1% $CaCO_3$. These plates were made by adding sterile 20% $CaCO_3$ to sterile R20-2 to a final concentration of 1%, mixing well, and dispensing 10 ml per plate. Final pH of the plate medium was 6.0.

Plates were incubated at 30° C. and scored after 7–10 days. Colonies that had no zones of clearing were picked for verification screen. The colonies were suspended in sterile test tubes that contained 2 ml of R20-2 medium and incubated three days to check for pellicle formation and drop in pH of the broth. Of 8100 colonies screened, two isolates from the 2% EMS treated sample were found to be gluconic acid negative; the better of them was designated as 1306-11.

Production of gluconic acid by 1306-11 and 1306-3 was determined in liquid R20-2glucose and Yl-glucose. Yl with 2% glucose had an initial pH of 4.21. The initial pH of R20-2 was 5.0.

A loopful of 1306-11 or 1306-3 culture from an R20-2 plate was suspended in 2 ml of Yl without carbon source. Cell counts for the suspensions were approximately $1.6 \times 10^8$ cells/ml. Tubes (16×125 mm) containing 3 ml of the appropriate medium were inoculated with 200 μl of the cell suspension and mixed well by vortexing. Tubes were incubated, without shaking, at 30° C. for three days.

Table 3 shows the pH and gluconate levels at day three for the mutant 1306-11 and for 1306-3, the parent strain. Values are shown for each of the duplicate tubes.

TABLE 3

Gluconate production by Acetobacter strains 1306-3 and 1306-11

|  | pH | | [GlcA], mM | |
|---|---|---|---|---|
| 1306-3 | | | | |
| R20-2 | 3.27 | 3.29 | 32.5 | 351 |
| Y1-Glc | 2.75 | 2.78 | 58.7 | 52.7 |
| 1306-11 | | | | |
| R20-2 | 5.11 | 5.11 | 0.096 | 0.066 |
| Y1-Glc | 3.57 | 3.61 | 0.963 | 0.963 |

EXAMPLE V

Preparation and Identification of Acetobacter strain 1306-21

Strain 1306-3 was mutagenized as described in Example III. Organisms were then plated out in CSL plates (2% glucose, 3% corn steep liquor) to establish single colonies. Colonies were picked and placed in microtiter tray wells containing 0.25 ml of CSL medium (4% glucose, 1% corn steep liquor). The trays were incubated 4–5 days until a clear drop in medium pH as measured with pH paper (range 2.9 to 5.2) was observed. Colonies whose pH was approximately 5 (pH paper green or greenish in color) were passed to a secondary screen.

In the secondary screen, selected colonies were inoculated into test tubes containing 2 ml of the high glucose medium used in the microtiter tray wells as described above. The tubes were incubated at 30° C. Colonies were examined for pellicle formation and pH. A gluconic acid negative strain designated 1306-21 was selected in this manner.

For comparison purposes, samples of strains 1306-11 and 1306-21 were grown in seed flasks containing CSL medium with varying amounts of glucose and corn steep liquor using the general procedure described in Example XI, infra. Cellulose production and medium pH were determined after five days of incubation. These determinations are reported in Table 4 below.

TABLE 4

Cellulose Production and pH of Acetobacter Strains 1306-11 and 1306-21

| | pH | | Cellulose (g/L) | |
|---|---|---|---|---|
| Medium | 1306-11 | 1306-21 | 1306-11 | 1306-21 |
| CSL 2,2* | 3.6 | 4.5 | 3.0 | 3.3 |
| CSL 4,2 | 3.1 | 3.4 | 2.9 | 4.8 |
| CSL 4,3 | 3.2 | 3.9 | 3.6 | 6.2 |

*numbers indicate % glucose, % corn steep liquor, respectively.

As reported, strain 1306-21 exhibited lower acid production (higher pHs) and greater cellulose production than did strain 1306-11 in these tests. The screening method described in Examples IV and V can also be used for selection of spontaneous mutants as well as wild strains from nature with low acid production.

EXAMPLE VI

Preparation of Reticulated Cellulose Product By Acetobacter Strain 1306-14

Strain 1306-14 was obtained by EMS mutagenesis (as described above in Example III) of Acetobacter strain 1306-11. It was identified as a large white mucoid colony on R20-2 plates whereas 1306-11 colonies are characteristically even, convex and dark beige in color.

A sample of 1306-14 from a frozen stock was inoculated into 100 ml R20-2 medium and was grown in static conditions at 30° C. for about three days. The entire contents of the culture were transferred to a sterile blender. Using a small blender head, the culture was blended with short five second bursts. A 5% (v/v) inoculum of the disrupted culture was transferred into 400 ml of R20-2 medium in a 2000 ml baffled flask, and was cultured with shaking at 125 rpm at 30° C. for about 2.5 day The contents of the flask were blended and were used to inoculate fermentors.

A 5% (v/v) inoculum of the disrupted culture from the baffled flasks was transferred into 9 l of R20-2 medium with 2% glucose. The fermentor (Braun) was equipped with an impeller; internal heating coils and baffles were removed. Fermentation conditions during the run were: 600 rpm initially and increased to 1000 rpm after 44 hours to increase mixing of the culture medium which had became viscous. Temperature was controlled at 30° C. (−1° C.+30° C.). The pH was controlled at 5.0±0.1 and oxygen concentration in the broth was maintained at about 30% of air saturation. At 48 hours the contents of the fermentor were collected. The cellulose was allowed to settle and excess liquid was poured off. The remaining cellulose was blended, washed and filtered as described above. The cellulose was washed with deionized (DI) water, extracted in 0.5M NaOH at 60° C. overnight. After the extraction the cellulose was washed with DI until the pH of the wash water dropped below 6.0. The preparation was used for scanning electron microscopic examination as described in Example VIII.

EXAMPLE VII

Preparation of Non-Reticulated Cellulose Product By Acetobacter Strain 1306-8 in Static Culture Strain 1306-8 is an Acetobacter isolate selected directly from a sample of NRRL B42. Colonies of 1306-8 are characterized by white, highly raised colonies on R20-2 plates. Strain 1306-8 produced gluconic acid. A sample of 1306-8 from a frozen stock (2.5 ml) was inoculated into 100 ml R20-2 medium and was cultured under static conditions at 30° C. in a 500 ml wide mouth Erlenmeyer flask. The seed culture was incubated about 2–4 days under these conditions until a visible pellicle formed. The entire contents of the seed culture were then blended and used to inoculate subsequent cultures.

Fermentation was carried out with wide-mouth Fernbach flasks containing 1 liter of R20-2 medium with 0.025 ml of a 10 g/100 ml suspension of Benlate fungicide (Dupont) in dimethyl formamide (DMF). This concentration of DMF and Benlate was effective to prevent fungal contamination without measurably affecting the growth of Acetobacter strain 1306-8.

About 8–10 ml was used to inoculate 1 liter of R20-2 culture medium. The cultures were grown in the Fernbach flasks for 10–14 days at 30° C. without agitation (i.e., standing cultures). At the time of harvest a 0.3 to 1.2 cm thick pellicles had formed.

Pellicles were removed from Fernbach flasks, then blended and washed with deionized water to remove media and part of the cells. Washing was done by filtration through a large buchner funnel using a filter screen (Spectramesh #146382) with mesh opening of 286 μM as a filter.

Extraction of blended and washed pellicle was carried out in 0.50M NaOH at about 60° C. for about 14 hours. After mixing and incubating for the desired period of time, the extraction mixture was filtered under the conditions described above. Washes with deionized $H_2O$ were continued until the pH of the wash water dropped below 6.0. The preparation was used for scanning electron microscopic examination as described below in Example VIII.

EXAMPLE VIII

Microscopic Examination of Cellulose Products

The cellulose products obtained in Examples VI and VII above were prepared for scanning electron microscopy (SEM). Specimens were freeze dried and then sputtered under vacuum with a 60:40 gold:palladium conductive film. Photomicrographs were taken using a Nanometrics scanning electron microscope operated at 16 Kv accelerating voltage.

Figure 2:
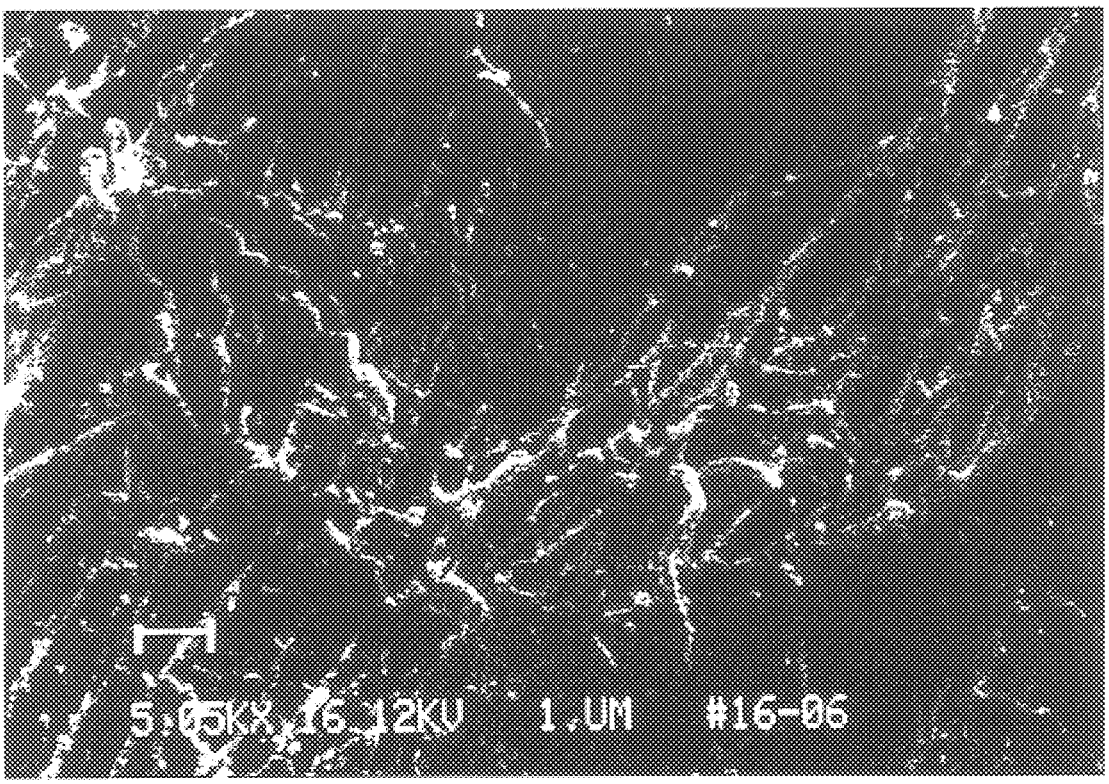
FIG. 2 is a scanning electron micrograph at magnification of 5000× of non-reticulated cellulose produced under non-agitated conditions.
Figure 4:
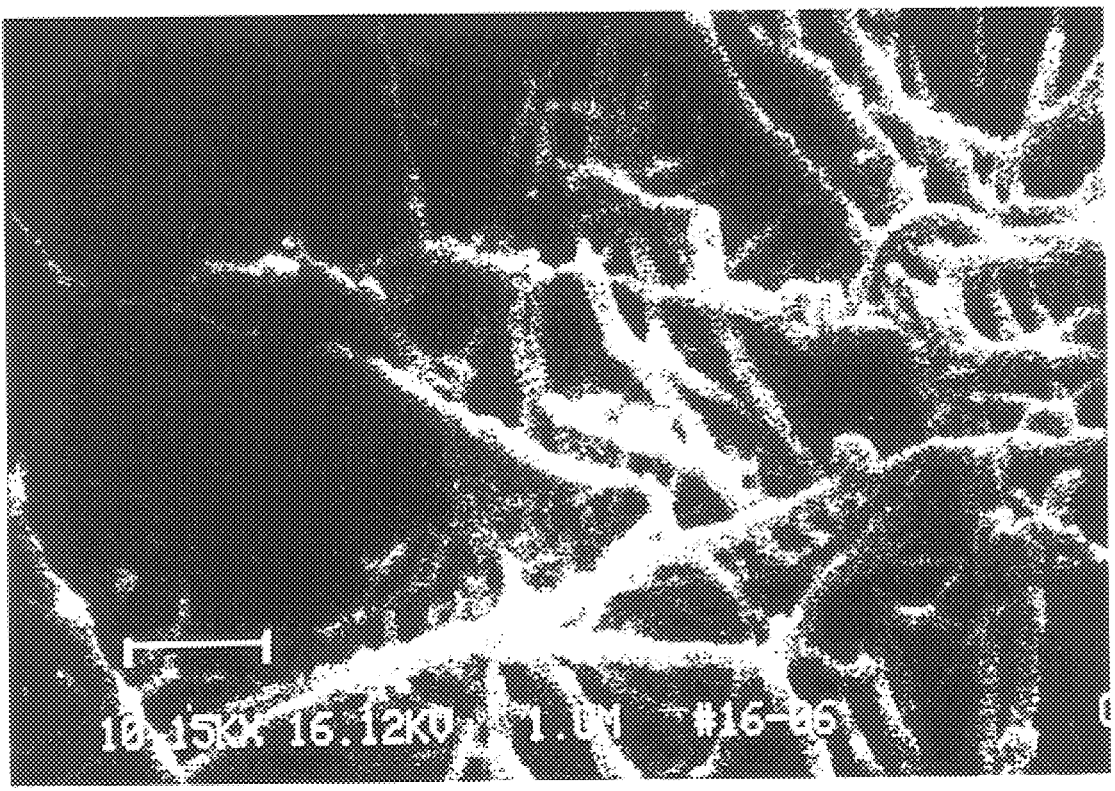
FIG. 4 is a scanning electron micrograph at a magnification of 10,150× of non-reticulated cellulose produced under non-agitated conditions.

FIGS. 2 and 4 are representative electron micrographs of the cellulose product obtained. FIGS. 2 and 4 show the cellulose product produced in static cultures according to Example VII. The figures show that the product consists predominantly of piles of extended cellulose fibrils that appear to overlap and cross one another but do not appear to interconnect. The filaments of cellulose produced under static conditions ranged in width from about 0.05 to 0.2 microns with many strands in the 0.05 to 0.1 micron range.

Figure 3:
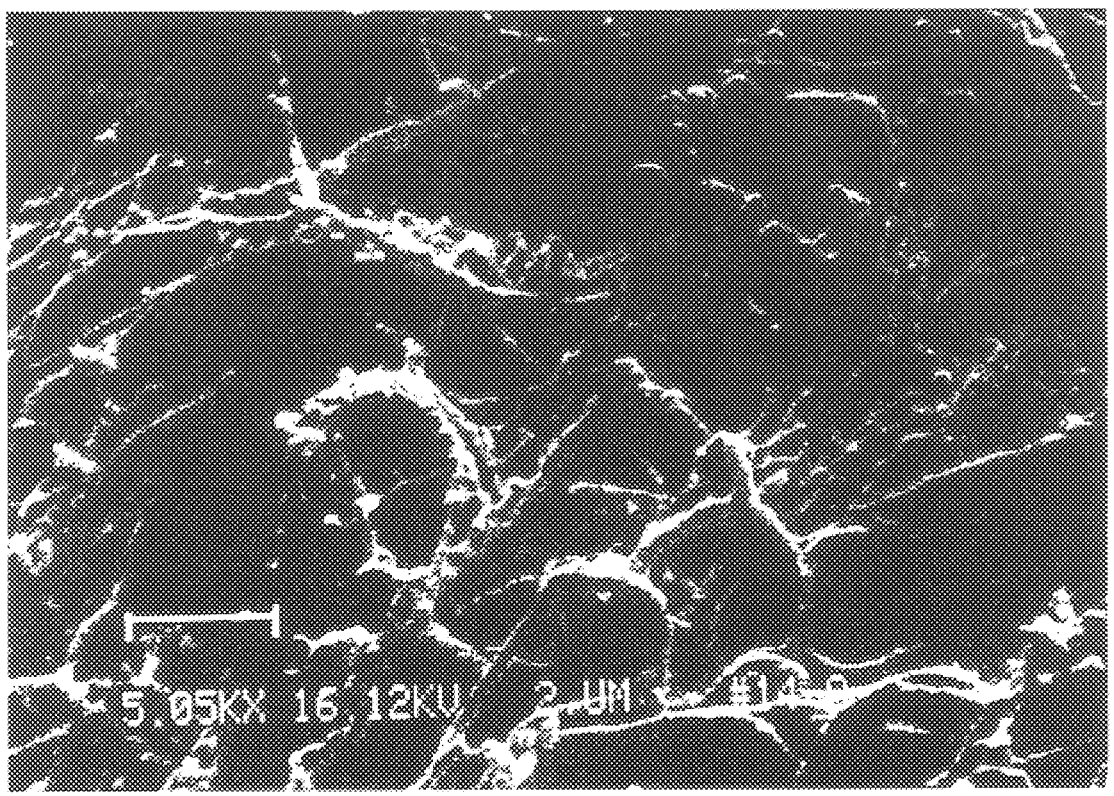
FIG. 3 is a scanning electron micrograph at a magnification of 5000× of the reticulated cellulose of the present invention.
Figure 5:
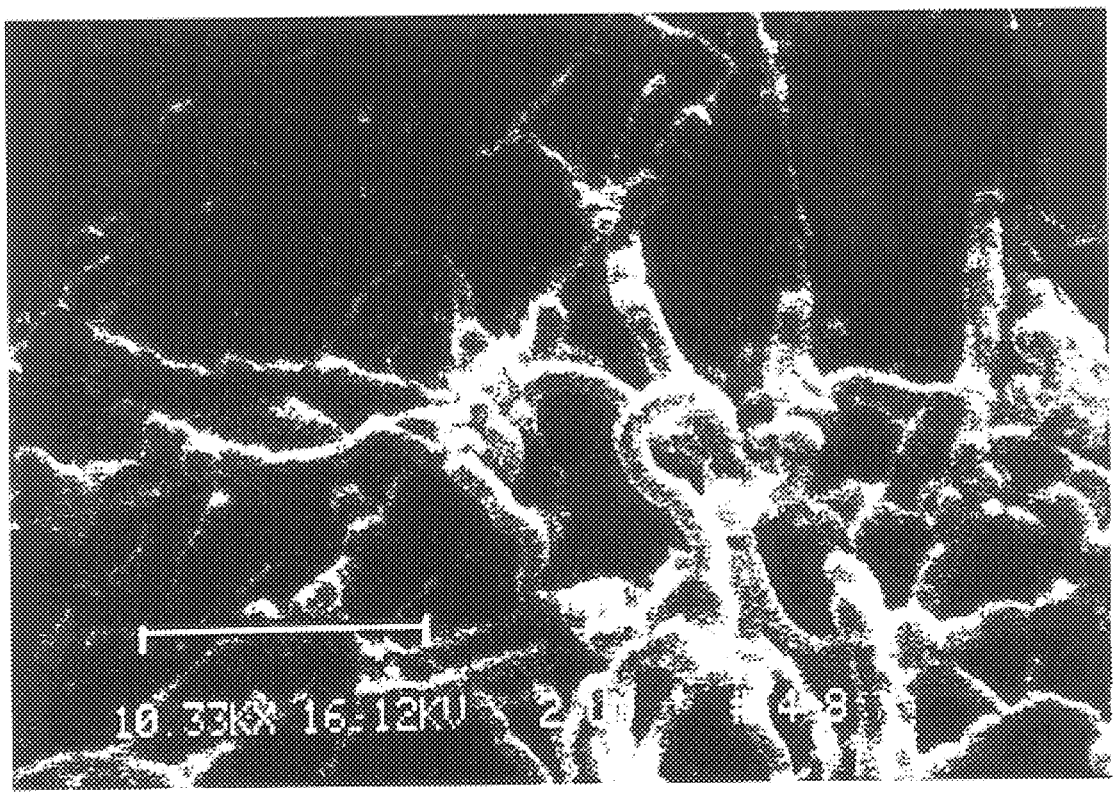
FIG. 5 is a scanning electron micrograph of a magnification of 10,330× of reticulated cellulose.

By contrast, FIGS. 3 and 5 show that the cellulose product produced in agitated culture in Example VI consists of a reticulum of fibrils that are generally thicker in cross section—in a range between 0.1 to 0.2 microns—than the cellulose grown in static culture. In addition the cellulose fibrils appear to form a network of predominantly interconnecting, rather than overlapping, fibrils.

EXAMPLE IX

Bacterial Cellulose products
Handsheets

This example shows some of the characteristics of the reticulated cellulose product according to the invention. Handsheets were prepared from samples of Acetobacter-produced cellulose to an approximate basis weight of 60 g/m² according to the procedure described in TAPPI official test method T205 om-81. Cellulose was produced from strain 1306-3 under static growth conditions in a flask culture using R20-medium with 2% glucose. Reticulated cellulose product was produced using strain 1306-11 in a fermentor under agitation with an impeller at 600 rpm using the same medium. The broth containing the cellulose was cold-stored prior to processing the cellulose. The cellulose was dispersed (1.2 g in 2 liters of water) in a British Disintegrator for 15,000 revolutions. The suspension was then poured into an automatic sheet mold containing a 200-mesh wire screen and allowed to drain at least two hours. The moist handsheet (15 cm in diameter) was removed from the sheet mold and initially pressed gently between blotters to remove excess water. The sheet was then placed in a TAPPI press between blotters for varying times under a 50 psi (345 kPa) load to produce sheets of various densities. Final drying of the sheets was done by passing them through a Noble and Wood laboratory drum dryer.

Tensile strength of sheets was measured according to TAPP: method T494 om-81 using an Instron Universal test instrument. The reticulated cellulose product of this Example was found to offer substantial resistance to densification when it was formed into a handsheet. By use of different wet pressing loads, a series of sheets was prepared having densities of about 300 to about 500 kg/m³. In spite of the low densities, these paper-like sheets have very high tensile strength. Typically, the tensile index for such sheets of the above density ranges is between 100 and 150 Newton meters/gram. Comparaole sheets formed from kraft pulp having densities below about 500 kg/m³ have virtually no tensile strength.

Handsheets formed from cellulose produced under static culture conditions do not exhibit the above-mentioned resistance to densification. Typically, such sheets from non-agitated cultures of cellulose have densities from about 500 to about 750 kg/m³ depending on the wet pressing load employed.

EXAMPLE X

Resistance to densification

This Example compares the resistance to densification of reticulated cellulose produced under agitated culture conditions and non-reticulated cellulose produced under static conditions in two Acetobacter strains. Reticulated cellulose was obtained using strain 1306-14 under agitated growth conditions as described in Example VI. Non-reticulated cellulose was obtained using strain 1306-3 in static flask cultures using R20-2 medium—2% glucose under essentially the same static conditions described in Example VII.

Handsheets were prepared from the reticulated cellulose and statically produced cellulose to an approximate weight basis of 60 g/m² as described in Example IX except that various pressing loads were used to produce the sheets. The density and other characteristics of sheets produced in this example from reticulated and non-reticulated cellulose are shown in Table 5.

TABLE 5

| Sample No. | Basis weight, g/m² | Thickness, mm | Density, kg/m³ | Pressing Method* |
|---|---|---|---|---|
| Non-reticulated cellulose | 56.9 | .106 | 538 | A |
| Reticulated cellulose | 55.3 | .219 | 252 | A |
| Non-reticulated cellulose | 60.3 | .080 | 753 | B |
| Reticulated cellulose | 67.9 | .157 | 433 | B |

*Method B includes higher pressing pressure than Method A.

EXAMPLE XI

Comparison of Cellulose Production By Various Acetobacter Strains

Six strains were tested. 1306-3 and 1306-11 were as described herein above. Two subcultures of *Acetobacter aceti subsp. xylinum* ATCC accession number 23769, designated herein as 23769A and 23769B were tested. In addition, ATCC strain 31174 and National Collection of Industrial Bacteria strain 8132 (Aberdeen, U.K.), and strain 1499-1 were also tested.

The growth medium for pre-seed culture, seed culture and production stages was CSL medium with 4% (w/v) fructose and 5% (w/v) CSL.

Pre-seed cultures were grown in 100 ml of the above-described medium in a 750 ml Falcon #3028 tissue culture flask with 0.01% Dow Corning antifoam under static conditions at 30° C. for 24 to 48 hours. The entire contents of the pre-seed culture was blended as described previously and was used to make a 5% (v/v) inoculum of the seed culture. Pre-seeds were streaked on R20-2 plates to check for contamination. All strains had homogeneous colony morphology except strain 1499 which had approximately 50% large colonies.

Seed cultures were grown in 25 ml of the above-described medium in baffled 125 ml flasks under shaking conditions in a reciprocal shaker at 125 rpm at 30° C. for three days. A sample from each of the blended seeds was streaked on R20-2 plates to check for contamination. All strains had homogeneous colony morphology except 1499-1 which had approximately 50% large colonies. The entire remaining contents of the seed culture was blended as described previously and was used to make a 5% inoculum for the production stage.

Duplicate fermentation flasks of each strain were grown in 125 ml baffled shake flasks on a reciprocal shaker at 125 rpm at 30° C. Duplicate flasks of each strain were harvested at days 1, 2, 3 and 4 except for ATCC strain 23769B which was harvested on day 7 due to poor growth. Strain 1499-1 and strain ATCC 31174 both produced a water soluble polysaccharide (WSP) under these conditions. No WSP was produced by strains 1306-3 or 1306-11.

Cellulose production was determined for each strain and is reported in Table 6. Values for cellulose production are in g/l.

TABLE 6

Cellulose Production for Various Strains*
5% CSL, 4% Fructose

| Strain | Day 1 | Day 2 | Day 3 | Day 4 |
|---|---|---|---|---|
| 1306-3 | 1.05 | 2.51 | 3.68 | 3.79 |
| 1306-11 | 1.25 | 3.09 | 4.45 | 5.55 |
| ATCC 23769A | 0.17 | 0.90 | 1.00 | 0.95 |
| ATCC 23769B | 0.13 | 0.54 | 0.62 | N.D.** |
| 1499-1 | 1.41 | 3.40 | 4.48 | 4.42 |
| NCIB 8132 | 0.46 | 0.99 | 1.43 | 1.92 |
| ATCC 31174 | 1.09 | 2.73 | 4.21 | 4.18 |

*Values for cellulose production are in g/l
**N.D. = not determined

EXAMPLE XII

Cellulose Production of Acetobacter Strain 1306-11 in Fermentors

Pre-seed and seed cultures of 1306-11 were grown as in Example XI for two days except that the medium contained 4% w/v glucose and 5% w/v CSL.

Seed cultures were grown in two liter baffled flasks in the same medium for two days except that the culture volume was 400 ml.

Two 14 l Chemap fermentors were run with a 5% (v/v) inoculum in initial 12 l volumes. During the 72 hour fermentor run, the cultures were maintained at about 30° C. (±1° C.).

In fermentor #1 the initial glucose concentration was 32 g/l. In fermentor #2 the initial glucose and sucrose concentrations were 10 g/l and 20 g/l, respectively. One hundred forty three g/l glucose was additionally added intermittently to fermentor #1 during fermentation. In fermentor #2, 50 g/l glucose and 72 g/l sucrose was added intermittently during fermentation.

The initial 2% v/v CSL concentration was augmented by the addition of an amount equivalent to 2% by volume of the initial volume at 32 hours and 59 hours.

The dissolved oxygen concentration was set at 30% air saturation. It fell in fermentor #2 to zero at hour 69 for about two hours of the fermentor run. Agitation was maintained initially at 600 rpm. As viscosity increased with increasing cellulose concentration, the impeller speed was increased to 1200 rpm. The concentrations of cellulose, gluconic acid, and 2-keto-gluconic acid are shown for fermentor 1 in Table 7. The concentration of cellulose is shown for fermentor 2 in Table 8. The maximum cellulose concentration reached in the glucose only fermentor #1 was 12.7 g/l. The maximum cellulose concentration reached in the glucose/sucrose fermentor #2 was 18.3 g/l. Both maxima were reached at 71.6 hours into the fermentation. The volumetric productivities at this time in fermentor #1 and #2 were 0.18 and 0.26 g/l/hr., respectively.

TABLE 7

Fermentor #1: 2% (v/v) CSL + 3.2% (w/v) Glucose (Initial)

| Hours | Cellulose g/l | Gluconic Acid g/l | 2-Keto-Gluconic Acid g/l |
|---|---|---|---|
| 0.5 | 0.1 | 0.09 | 0.5 |
| 8.0 | 0.3 | 0.21 | — |
| 18.0 | 1.6 | 0.38 | 1.0 |
| 22.5 | 2.8 | 0.53 | 2.0 |
| 28.2 | 4.6 | 0.91 | 3.4 |
| 32.8 | 5.7 | 1.29 | 5.0 |
| 42.2 | 7.9 | 2.71 | — |
| 45.7 | 9.3 | 4.28 | 14.6 |
| 51.5 | — | 5.92 | — |
| 55.8 | 11.2 | — | — |
| 57.3 | 11.1 | 7.27 | 25.5 |
| 69.0 | 11.3 | 9.01 | 35.0 |
| 71.6 | 12.7 | 9.29 | 36.9 |

TABLE 8

Fermentor #2: 2% (v/v) CSL + 1% (w/v) Glucose + 2% (w/v) Sucrose (Initial)

| Hours | Cellulose g/l |
|---|---|
| 0.5 | 0.2 |
| 8.0 | 0.4 |
| 18.0 | 1.5 |
| 22.5 | 2.7 |
| 28.3 | 4.4 |
| 32.9 | 6.1 |
| 42.2 | |
| 45.8 | 10.5 |
| 51.5 | 13.0 |
| 55.8 | |
| 57.3 | 14.5 |
| 69.0 | 17.0 |
| 71.6 | 18.3 |

EXAMPLE XIII

Cellulose Production By Acetobacter Strain 1306-21 in Fermentors

The fermentation described in Example XII was repeated using strain 1306-21 in place of 1306-11 and with the following changes:

1. The preseed and seed were prepared in CSL medium with 2% glucose, 2% corn steep liquor.
2. The agitation rate did not exceed 900 rpm.
3. The initial glucose concentration was 20 g/l, and 109 g/l more were added during the run.
4. Initial CSL concentration was 2% v/v and 2% v/v more were added after 27.8 hours in the run.

The concentrations of cellulose, gluconic acid, 2-ketogluconic acid and 5-keto-gluconic acid observed in this run are reported in Table 9.

TABLE 9

14-L Chemap Fermentation: Strain 1306-21

| Hours | Cellulose g/l | Gluconic Acid g/l | 2-Keto-gluconic Acidg/l | 5-Keto-gluconic Acid g/l |
|---|---|---|---|---|
| 0.5 | 0.18 | N.D. | N.D. | N.D. |
| 13.3 | 0.60 | N.D. | N.D. | N.D. |
| 20.8 | 1.75 | N.D. | N.D. | N.D. |
| 27.8 | 2.55 | N.D. | N.D. | N.D. |
| 37.1 | 5.67 | N.D. | N.D. | N.D. |
| 44.8 | 8.74 | N.D. | N.D. | N.D. |
| 52.2 | 10.90 | N.D. | N.D. | N.D. |
| 59.0 | 12.76 | 0.80 | N.D. | N.D. |

N.D. ≦ 0.5 g/l

Comparing the results of Table 9 with those of Table 7, it appears that strain 1306-21 is equal to or better than strain 1306-11 as regards cellulose production while producing much less acid. Lower acid production should, in theory, permit strain 1306-21 to be grown to comparable concentrations with less base addition.

EXAMPLE XIV

Effects of Agitation on Cellulose Properties

Two sets of tests were carried out to assess the effect of agitation on the following four properties:

1. Handsheet formation (TAPPI test of Example IX): the ability of purified, treated and resuspended cellulose fibers from the fermentation to form an integral sheet on a 150 mesh screen. The results are judged according to the percent of the resuspended fibers retained on the screen (% cellulose retention) and to a qualitative assessment of the integrity of the sheet formed.

2. Settling rate: the rate at which a diluted sample of cellulose from the fermentor settles in a graduated cylinder. The decreasing height of the sediment/supernatant interface of the settling suspension of cellulose is plotted versus time. The instantaneous settling rate can be determined from the slope of the plot at a given time. This property depends on the cellulose particle size and density.

3. Suspension viscosity: the viscosity of suspended cellulose fermentor broth measured by a Thomas-Sormer viscometer calibrated with glycerol solutions. This property depends on the morphology of the cellulose particles.

4. Particle size and morphology: This property is determined from photomicrographs of cellulose from the fermentor.

The first set of tests consisted of four fermentor runs, using Acetobacter strain 1306-11, during which samples were withdrawn as a function of time from 14 liter Chemap fermentors operated at varying rates of maximum agitation. These four fermentor runs were typical fermentations with growing cultures, but extended past normal fermentation times to allow evaluation of the effect of agitation over prolonged time. Samples from these runs were analyzed for handsheet formation ability.

The second set of experiments, also using Acetobacter strain 1306-11, consisted of agitating old, non-growing cellulose cultures, harvested from a 250 liter fermentor run, in four 14 liter Chemap fermentors. The agitation rate was constant in each fermentor, but was varied among fermentors. Samples were taken with respect to time from each fermentor. The cellulose concentration in this set of experiments was uniform in all the fermentors, but was approximately half the concentration of the final concentrations in the first set of experiments. In this second set of experiments, nitrogen was sparged at about average gassing rate (air and oxygen) of the first set of experiments. Samples from the second set of experiments were analyzed for handsheet formation, settling rate, viscosity, and particle size and morphology.

Handsheet results from the first and second sets of experiments are summarized in Tables 10 and 11, respectively.

TABLE 10

| Agitation Rate (rpm) | Time at This Agitation Rate (hr) | Sheet Formation | % Cellulose Retention |
|---|---|---|---|
| 700 | 16 | Good* | 100 |
|  | 38 | Good* | 92 |
|  | 81 | Poor* | 64 |
| 750 | 16 | Good* | 94 |
|  | 37 | Good* | 101 |
|  | 81 | Poor* | 55 |
| 800 | 16 | Good* | 109 |
|  | 38 | Poor* | 90 |
|  | 81 | Poor* | 84 |
| 1,000 | 0 | Good | 102 |
|  | 23 | Poor | 38 |
|  | 50 | None | 0 |
|  | 64 | None | 0 |

*These sheets had a target weight of 0.65 to 0.75 g cellulose instead of the usual 1.2 g, which was the target weight for the 1000 rpm run.

TABLE 11

| Agitation Rate (rpm) | Time at This Agitation Rate (hr) | Sheet Formation* | % Cellulose Retention |
|---|---|---|---|
| 600 | 16 | Good | 96 |
|  | 40 | Good | 99* |
|  | 63 | Good | 89 |
|  | 86 | Good | 88 |
| 700 | 16 | Good | 92 |
|  | 40 | Good | 89 |
|  | 63 | Good | 88 |
|  | 86 | Good | 89 |
| 800 | 16 | Good | 90 |
|  | 40 | Good | 86 |
|  | 63 | Good | 100 |
|  | 86 | Good | 92 |
| 1,000 | 16 | Good | 81 |
|  | 27 | Good | 96 |
|  | 50 | Poor | 73 |
|  | 73 | Poor | 78 |

*All of these sheets had a target weight of 1.2 g.

Table 10 shows that handsheet formation may be adversely affected by both increased agitation rate and increased time of agitation.

The results in Table 11 in which more dilute and non-growing cellulose cultures were used showed handsheet formation to be not as sensitive to the agitation rate and time as shown in Table 10. Good handsheets could be made up to 86 hours at 800 rpm or 27 hours at 1000 rpm agitation. The better results in Table 11 may be due to lower cellulose concentration in the fermentor or higher target sheet weights. In addition the pellets may have been more resilient to start with due to different fermentation conditions.

Other test results do, however, show cellulose properties being affected by agitation rate and time during the second set of experiments. For instance, the viscosity analyses indicate increasing viscosity of the cellulose suspension in the fermentor with agitation time at 800 and 1000 rpm. The increased viscosity may reflect the change in the morphology of the cellulose from dense pellets to a less densely packed fiberlike form. Such changes were observed in the photomicrographs used to evaluate particle size and morphology.

The settling rate studies showed that cellulose agitated at higher rates or for longer times settled more slowly. These results were consistent with the photomicrographs which showed that with increased agitation rate and time the cellulose pellets appear fragmented into smaller particles as determined by light microscopy. The results from analyses of the settling rates, viscosities, particle size and form, and handsheet formation, all appear generally consistent and to some extent, correlate with each other.

The mechanism of change of the cellulose properties with agitation rate and time is not understood completely at this time. It is known that increased agitation rates increase the shear stress on the cellulose particles. However, other forces may also be contributing to the changing cellulose properties; examples include turbulent eddy stresses and flocculating pressures. Furthermore, the above forces and stresses, as well as others, are also exerted during recovery and purification of the cellulose. Accordingly, caution must be exercised during all stages of cellulose processing to minimize damage to the cellulose.

EXAMPLE XV

The Effect of Citrate, Nitrilotriacetic Acid, and Ferric Iron on Acetobacter Growth Acetobacter strain 1306-21 was adapted to growth in the absence of vitamins in the medium. The adaptation was made by subculturing it 20 times in AMM (R-70) w/out vitamins. The basal medium used in the experiment was AMM w/out vitamins+3% (w/v) glucose, 25 mM 3,5-dimethyl glutaric acid (DMG), 1 $\mu$M CoCl2, and 1 $\mu$M NiCl2.

The preseed for the experiment was grown in basal medium in standing flasks for 48 hr. The seed was grown in basal medium for 72 hr (30° C., 125 rpm). All test flasks received a 6% (v/v) inoculum. The flasks were incubated at 30° C., 125 rpm, and harvested after three days. Biomass analysis (cellulose+cells) was used to follow cell growth. Cells plus cellulose were centrifuged, washed with deionized water and dried in a vacuum oven at 80° C. to a constant weight.

The results are shown in Table 12. Although there are some major differences between duplicate flasks, the results show that all of the test systems had significantly more growth than did the basal medium control. The addition of ferric iron salt stimulated growth as well as the addition of citrate or nitrilotriacetic acid (NTA). Both citrate and NTA are known to be strong chelators of ferrous and ferric ions.

TABLE 12

The Effect of Citrate, Nitrilotriacetic Acid, and Ferric Iron on Acetobacter Growth

|  | Biomass (g/L) | Average Biomass (g/L) |
|---|---|---|
| Basal Alone | 0.820 | 0.774 |
|  | 0.726 |  |
| Basal + 5 mM Citrate | 2.404 | 1.912 |
|  | 1.420 |  |
| Basal + 10 $\mu$M FeCl$_3$ | 0.952 | 1.280 |
|  | 1.608 |  |
| Basal + 1 mM Citrate + 10 M FeCl$_3$ | 2.308 | 1.888 |
|  | 1.468 |  |
| Basal + 1 mM Nitrilotriacetic Acid | 1.756 | 1.616 |
|  | 1.476 |  |
| Basal + 0.2% Peptone | 1.640 | 1.582 |
|  | 1.524 |  |
| Basal + 0.3% TYE | 2.464 | 2.416 |
|  | 2.368 |  |

EXAMPLE XVI

Evaluation of a New Medium (R70-2)

The previous example (XV) suggested that iron is limiting in AMM (R70) medium. The precipitate that has been observed in this medium may be iron phosphate. Addition of iron chelators like citric acid or nitrilotriacetic acid prevents the precipitation of iron and enhances growth. On the basis of these findings a new medium was formulated with 4 mM (Na)citrate. The purpose of this study was to evaluate Acetobacter growth in the new medium (R70-2) compared to the old medium (R70).

The ingredients of AMM (R70) and R70-2 are set forth above. The new medium (R70-2) had the following changes relative to R70:

1. 0.010 mM FeCl$_3$ was used instead of 0.013 mM FeSO$_4$;
2. 4 mM citrate was present;
3. 0.001 mM CoCl$_2$ was present;
4. 0.001 mM NiCl$_2$ was present;
5. CuSO$_4$ was increased from 0.0002 mM to 0.001 mM;
6. ZnSO$_4$ was decreased from 0.006 mM to 0.005 mM; and
7. MnSO$_4$ was decreased from 0.006 mM to 0.005 mM The (NH$_4$)$_2$SO$_4$, KH$_2$PO$_4$, MgSO$_4$ and citrate were prepared at 1× concentration and steam sterilized. The trace metal solution (including iron) and the vitamin mix were prepared at 100× concentration, filter sterilized, and added aseptically.

The Acetobacter strain used was 1306-21. The preseed for this experiment was grown for 48 hr in R70-2 containing 2% (w/v) glucose, 0.2% (w/v) technical grade extract, Amberex 1003 (Universal Food, WI), (TYE) and 25 mM DMG. The seed was grown for 72 hours in R70-2 with 2% glucose, 0.1% (w/v) TYE and 25 mM DMG. The test flasks had 2% (w/v) glucose and 25 mM DMG. The inoculum was 5% (v/v), and the flasks were incubated at 30° C. and 125 rpm. Biomass measurements were used to follow cell growth.

Figure 6:
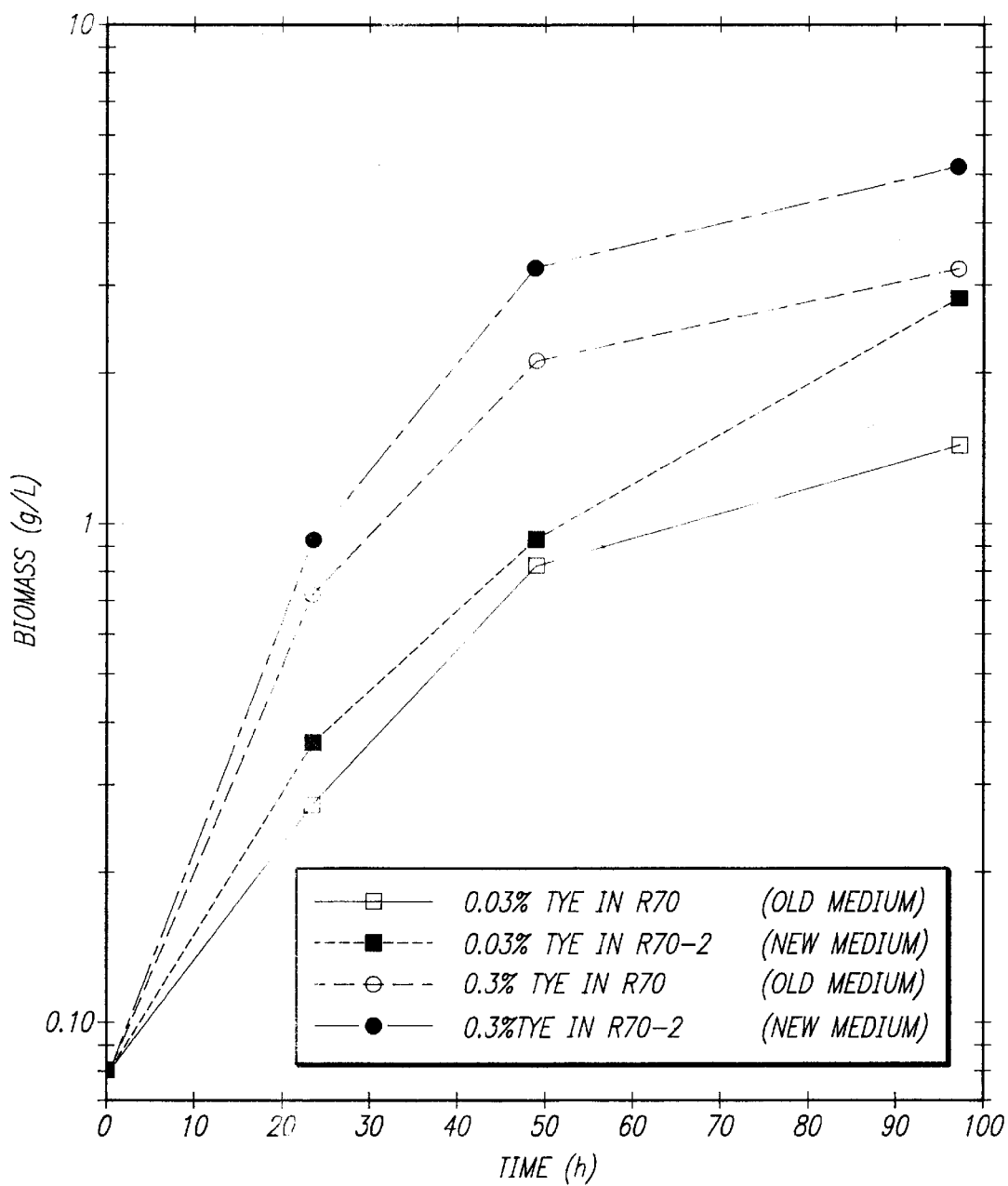
FIG. 6 is a graph showing growth (increase in biomass) of Acetobacter strain 1306-21 in various media as described in Example XVI, infra.

The results are shown in FIG. 6. At both low and moderate yeast extract concentrations, the new medium supported significantly higher levels of growth than R70 medium. The 0.3% TYE R70-2 flasks were glucose-limited on day 4 (less than 0.1% glucose was present). Higher levels of biomass may be obtainable if the glucose is kept in excess. All of the other systems contained excess glucose.

The R70-2 plus 0.03% TYE did not reach stationary phase even after 4 days of incubation. The pH of the day 4 flasks was 3.8 to 4.0. Presumably, the pH of the medium would start to inhibit growth if the flasks were left on the shaker for a longer period of time.

EXAMPLE XVII

Cellulose Production with Technical Grade Yeast Extract (TYE) as a Complex Nitrogen Source This Example compares cellulose production by Acetobacter on 0.4% TYE versus 0.4% TYE plus 0.1% CSL.

The basal fermentor medium was R70-2 medium with the following modifications:

1. The $(NH_4)_2SO_4$ was decreased to 12.5 mM;
2. Initial glucose concentration was 2% (w/v);
3. 0.4% (w/v) TYE (Amberex 1003, Universal Foods) was added to both fermentors;
4. 0.1% (v/v) CSL was added to one of the fermentors before inoculation; and
5. Initial concentrations of phosphate, magnesium, and calcium were doubled.

Acetobacter strain 1306-21 was used for both fermentors. The seed was grown according to standard procedures in R70-2 with 3% glucose, 25 mM DMG, and 0.5% TYE. Both seed stages were grown for 2 days before transfer.

$NH_4OH$ (4N) was used to titrate acid production during the fermentor run as well as to supply additional inorganic nitrogen. Glucose addition was linked to the base addition to maintain a more even glucose concentration. The fermentors used were 14-L Chemap (Switzerland) fermentors.

Tables 13 and 14 show the kinetics of cellulose production with 0.4% TYE and 0.1% CSL, respectively. The results demonstrate that TYE can be an effective complex nitrogen source and that addition of CSL enhances cellulose production.

TABLE 13

Cellulose Production with 0.4% TYE

| Time (hr) | Cellulose (g/l) |
|---|---|
| 0.81 | 0.19 |
| 19.72 | 0.71 |
| 28.32 | 1.19 |
| 34.90 | 1.62 |
| 43.92 | 2.19 |

TABLE 14

Cellulose Production with 0.4% TYE and 0.1% CSL

| Time (hr) | Cellulose (g/l) |
|---|---|
| 0.83 | 0.19 |
| 19.69 | 1.59 |
| 24.64 | 2.67 |
| 29.60 | 4.68 |
| 34.87 | 6.16 |
| 43.92 | 6.97 |

EXAMPLE XVIII

Cellulose Production with Sheftone F as a Complex Nitrogen Source

Shake flask experiments identified Sheftone F (Sheffield, Norwich, N.Y.) as an effective complex nitrogen source for cellulose production. This Example compares cellulose production using 1% Sheftone F and 0.2% TYE versus 1% Sheftone F plus 0.2% CSL as a complex nitrogen source in fermentors.

The basal fermentor medium was R70-2 with the following modifications:

1. The $(NH_4)_2SO_4$ was decreased to 12.5 mM;
2. Initial glucose concentration was 2% (w/v);
3. 1.0% (w/v) Sheftone F was added to both fermentors;
4. 0.2% (w/v) TYE was added to one fermentor;
5. 0.2% (v/v) CSL was added to the second fermentor; and
6. Initial concentrations of phosphate, magnesium, and calcium were doubled.

Acetobacter strain 1306-21 was used for both fermentors. The strain was grown as described in Example XVII in R70-2 with 3% (w/v) glucose, 25 mM DMG, and 0.5% (w/v) TYE. Both seed stages were grown for 2 days before transfer.

$NH_4OH$ (4N) was used to titrate acid production during the fermentor run as well as to supply additional inorganic nitrogen. Glucose addition was linked to the base addition to maintain a more even glucose concentration. The fermentors used were 14-L Chemap fermentors.

The kinetics of cellulose production on 1% Sheftone F supplemented with 0.2% TYE or CSL are presented in Tables 15 and 16, respectively. These results demonstrate that Sheftone F is an effective complex nitrogen source for cellulose production.

TABLE 15

Cellulose Production with 1% Sheftone and 0.2% TYE

| Time (hr) | Cellulose (g/l) |
|---|---|
| 0.73 | 0.07 |
| 17.47 | 0.64 |
| 21.56 | 1.12 |
| 25.97 | 1.81 |
| 30.66 | 2.85 |
| 40.93 | 6.33 |
| 48.11 | 7.68 |
| 55.35 | 10.53 |
| 66.15 | 9.97 |

TABLE 16

Cellulose Production with 1% Sheftone and 0.2% CSL

| Time (hr) | Cellulose (g/l) |
|---|---|
| 0.76 | 0.09 |
| 17.58 | 0.66 |
| 21.48 | 1.14 |
| 26.18 | 1.89 |
| 30.71 | 2.91 |
| 41.27 | 6.69 |
| 48.09 | 8.26 |
| 55.40 | 10.49 |
| 66.30 | 11.16 |

EXAMPLE XIX

C-13 NMR Analysis of Cellulose Products

The microstructure of the bacterial cellulose produced under agitated conditions (as described in Table 19) was examined and compared to that of bacterial cellulose produced under non-agitated or static culture conditions. NMR spectrometry was performed essentially as described by Vanderhart et al., in *Macromolecules* 17:1465–1472 (1984), incorporated by reference herein, except with certain modifications. Thus, NMR spectrometry was performed using an S-100 NMR spectrometer (General Electric, Fremont, Calif.) operating at 2.34 T, which corresponds to frequencies of 100.2 MHz for protons and 25.2 MHz for C-13. Cross-polarization times were typically 1.0 to 2.0 ms.

The respective radiofrequency amplitudes were set for a Hartmann-Hahn match at a rotating-frame precision frequency of 43 kHz, and not mismatched by the sample spinning frequency. The magic-angle spinning rate was 2800-3100 rps. Chemical shift referencing was accomplished by setting operating frequencies daily so that the methyl carbon resonance of hexamethylbenzene appeared at 17.80 ppm. The rotor material was boron nitride or phase-stabilized zirconia.

The NMR results for the samples tested are set out in Tables 17 and 18 below and consisted of cellulose produced by five (5) non-agitated Acetobacter cultures and from eleven (11) Acetobacter cultures that were cultured in fermentors. The strains used and culture conditions corresponding to the sample numbers in Tables 17 and 18 are set forth in Table 19.

Tables 17 and 18 present the resulting morphology distribution obtained by NMR analysis of the samples indicated therein from strains cultured statically and in agitated culture. These results show that there are important differences between cellulose produced from fermentor samples (agitated) compared to that from static culture. The lower crystallinities (cellulose I) of agitated samples are supported by the substantial changes in the amounts of the $I_\alpha$ and $I_\beta$ spectrum peaks and the peaks due to amorphous cellulose. Especially noteworthy is the consistent presence of cellulose II in all fermentor samples and its absence (except for sample A-008 corresponding to Acetobacter strain 1307) in static culture samples. In addition, in two agitated samples (samples A-070 and A-071 corresponding to Acetobacter strain 1306-11), subject to long fermentation times and thus high shear stress, a significant portion of the cellulose is cellulose II, suggesting a relationship between cellulose II content and the amount of agitation in culture. There was also a consistent difference between the $I_\alpha$ content in static as compared to agitated cultures. In addition, a higher level of residual signal occurs at 90 ppm in cellulose from agitated culture. As shown in Tables 17 and 18 the method provides excellent agreement between the two determinations of amorphous cellulose content.

Although not wishing to be limited by any particular explanation, the differences observed herein using NMR analysis may reflect the manner in which individual cellulose molecules are packed together and to conformational differences between different molecular chains.

TABLE 17

NMR Studies Of Bacterial Cellulose Morphology
Static Culture Samples
MOLE % (AVG. DEVIATION) OF CRYSTALLITE

| SAMPLE | $I_\alpha$ | $I_\beta$ | II | RESIDUAL* | AMORPHOUS SUB | C-4 |
|---|---|---|---|---|---|---|
| A-007 | 40 (1) | 26 (2) | — | 4 (1) | 29 (<1) | 29 |
| A-008 | 34 (<1) | 21 (<1) | 7 (2) | 6 (1) | 32 (<1) | 32 (1) |
| A-009 | 42 | 25 | — | 3 | 30 | 29 |
| A-010 | 2 (1) | 28 (1) | — | 2 | 28 (<1) | 26 (<1) |
| A-012-3 | 38 (<1) | 27 (<1) | — | 4 | 31 (<1) | 31 (<1) |
| Subspectrum Sources | | | | | | |
| A-012-6 (also static) | 42 | 30 | — | — | 28 | 27 |
| Whatman CF-1 (from Cotton) | 16 | 51 | — | — | 33 | 33 |

*Residual Component at 90 PPM
—Not detectable

TABLE 18

NMR Studies Of Bacterial Cellulose Morphology
Fermenter (Agitated) Samples
MOLE % (AVG. DEVIATION) OF CRYSTALLITE

| SAMPLE | $I_\alpha$ | $I_\beta$ | II | RESIDUAL* | AMORPHOUS SUB | C-4 |
|---|---|---|---|---|---|---|
| A-070 | 19 | 15 | 24 | 7 | 35 | 38 |
| A-071 | 19 | 18 | 25 | 4 | 34 | 34 |
| A-072 | 23 (1) | 24 (1) | 6 (2) | 10 (1) | 37 (<1) | 38 (1) |
| A-075 | 22 (<1) | 19 (<1) | 8 (1) | 11 (2) | 40 (1) | 38 |
| A-076 | 22 | 23 | 15 | 4 | 36 | 37 |
| A-085 | 29 | 26 | 8 | 4 | 32 | 31 |
| A-091 | 22 | 19 | 12 | 11 | 36 | 35 |
| A-092 | 22 | 17 | 12 | 14 | 3S | 37 |
| A-095 | 25 | 21 | 6 | 14 | 34 | 35 |
| A-125 | 23 | 16 | 13 | 12 | 36 | 36 |
| A-126 | 30 | 23 | 6 | 8 | 34 | 32 |

*Residual Component at 90 PPM

TABLE 19

Strains And Culture Conditions For NMR Studies Of Bacterial Cellulose Morphology

| Sample Number | Strain Source | Fermentation Conditions | Post Fermentation Treatment |
|---|---|---|---|
| A-007 | 1306-3 | f,st,G/R20 | 0.8M NaOH, 32° C., 12 h |
| A-008 | 1307 sm2[1] | " | 0.5M NaOH, 60° C., 1 h |
| A-009 | 1499-1 | " | 0.5M NaOH, 50° C., 12 h |
| A-010 | 1306-3 | " | 0.5M NaOH, 60° C., 16 h |
| A-012 | 1306-8 | " | 0.5M NaOH, 60° C., 1 h |
| A-070 | 1306-11 | F/600–1000 rpm G + CSL | 0.5M NaOH, 60° C., 2h |
| A-071 | 1306-11 | F/600–1200 rpm G + S + CSL | 0.5M NaOH, 60° C., 2 h |
| A-075 | 1306-11 | F/600–1100 rpm S + CSL | 0.5M NaOH, 60° C., 2 h |
| A-076 | 1306-11 | F/600–950 rpm F + CSL | 0.5M NaOH, 60° C., 2 h |
| A-085 | 1306-11 | 250 L/100–185 rpm G + CSL | 0.1N NaOH, 60° C., 2 h |
| A-091 | 1306-11 | F/600–1000 rmp G + CSL | 0.1N NaOH, 65° C., 2 h |
| A-092 | 1306-11 | F/600–1000 rpm G + CSL | 0.1N NaOH, 65° C., 2 h |
| A-095 | 1306-11 | 750 L/100–150 rpm G + CSL | 0.1N NaOH, 65° C., 2 h followed by light column washing and thorough washing in filter press |
| A-125 | 1306-11 | 250 L/100–175 rpm G + CSL | 0.1N NaOH, 65° C.; 2 h |
| A-126 | 1306-11 | 6000 L/40–60 rpm G + CSL | 0.1N NaOH, 65° C., 3.5 h large-scale preparation |

Abbreviations: f = flask; F = fermentor; st = static; G = glucose; S = sucrose;. F = fructose; CSL = corn steep liquor; 250 L = 250 L fermentor
[1]Strain 1307 sm2 was a variant of Acetobacter strain. 1307

It will be appreciated from the foregoing that bacterial cellulose may be produced at high efficiency under agitated conditions for sustained periods of time. Heretofore the sustained production of bacterial cellulose at high productivity has been fraught with difficulties and extremely low productivities. The invention disclosed herein and claimed below clearly represents a major advance in fermentative production of bacterial cellulose.

Deposits

Samples of strains 1306-3, 1306-11, 1306-21, 1306-8 and 1306-14 were deposited under the terms of the Budapest Treaty on the international Recognition of the Deposit of Microorganisms for the Purposes of Pat. Procedure and Regulations thereunder at the American Type Culture Collection, 12301 Parklawn Drive, Rockville, Md. USA 20832. Deposit dates and accession numbers are given below:

| Strain | Accession No. | Deposit Date |
|---|---|---|
| 1306-3 | 53264 | September 13, 1985 |
| 1306-11 | 53263 | September 13, 1985 |
| 1306-21 | 53524 | July 25, 1986 |
| 1306-8 | 53749 | March 1, 1988 |
| 1306-14 | 53750 | March 1, 1988 |

Said deposits were made pursuant to a contract between the ATCC and the assignee of this patent application. The contract with the ATCC provides for permanent availability of said strains and progeny thereof to the public upon issuance of a U.S. patent related to this application describing and identifying the deposit or upon the publication or laying open to the public of any U.S. or foreign patent application, whichever comes first, and for the availability of these strains and the progeny thereof to one determined by the U.S. Commissioner of Pat.s and Trademarks to be entitled thereto according to 35 USC §122 and the Commissioner's rules pursuant thereto (including 37 CFR §1.14 with particular reference to 886 OG 638). The assignee of the present application has agreed that if the strains on deposit should die or be lost or destroyed when cultivated under suitable conditions, it will be promptly replaced upon notification with a viable culture of the same strain.

The deposits under the terms of the Budapest Treaty assures that said cultures deposited will be maintained in a viable and uncontaminated condition for a period of at least five years after the most recent request for the furnishing of a sample of the deposited microorganism was received by the ATCC and, in any case, for a period of at least 30 years after the date of the deposit.

Availability of the deposited strains is not to be construed as a license to practice the invention in contravention of the rights granted under the authority of any government in accordance with its patent laws.

Also, the present invention is not to be considered limited in scope by the strains deposited, since the deposited embodiments are intended only to be illustrative of particular aspects of the invention. Any micro-organism strains which are functionally equivalent to those deposited are considered to be within the scope of this invention. Further, various modifications of the invention in addition to those shown and described herein apparent to those skilled in the art from the preceding description are considered to fall within the scope of the appended claims.

With the information contained herein, various departures from the precise description of the invention will be readily apparent to those skilled in the art to which the invention pertains without departing from the spirit of the invention claimed below.

What is claimed is:

1. A biologically pure strain of Acetobacter, or progeny thereof capable of producing a reticulated cellulose product under agitated culture conditions that are sufficient to prevent pellicle formation, said Acetobacter having a frequency of change from cellulose producing forms to cellulose non-producing forms of less than 0.5% over the course of 42–45 generations when grown under said agitated culture conditions, as determined by observing the colony morphology of cells from said agitated culture on solid medium and wherein said reticulated cellulose produced comprises a cellulose II form content of from about 6% to about 25% of total cellulose produced as measured by nuclear magnetic resonance.

2. The strain of claim 1, wherein said strain produces said reticulated cellulose at an average volumetric productivity of at least 0.1 grams/liter/hour when grown under said agitated culture conditions.

3. A biologically pure strain of Acetobacter, or progeny thereof derived from and having the ability of microorganisms selected from the group consisting of Acetobacter strains ATCC Nos. 53264, 53263 and 53524 to produce a reticulated cellulose producing formation, Acetobacter strain having a frequency of change from cellulose producing forms to cellulose non-producing forms of less than 0.5% over the course of 42–45 generations when grown under said agitated culture conditions as determined by observing the colony morphology of cells from said agitated culture on solid medium, said reticulated cellulose produced comprises a cellulose II form content of from 6% to about 25% of total cellulose produced as measured by nuclear magnetic resonance, and wherein said strain produces reduced amounts of gluconic acid and ketogluconic acids when grown in a glucose-containing medium.

4. The strain of claim 3, further having the ability to produce said reticulated cellulose at an average volumetric productivity of at least 0.1 grams/liter/hour when grown under said agitated culture conditions.

* * * * *